US006884896B2

(12) United States Patent
Saitoh et al.

(10) Patent No.: US 6,884,896 B2
(45) Date of Patent: Apr. 26, 2005

(54) BENZO[B]THIOPHENE DERIVATIVES AND PROCESS FOR PREPARING THE SAME

(75) Inventors: Hiroshi Saitoh, Hino (JP); Naoki Tsuchiya, Hino (JP); Tsuyoshi Mizuno, Hino (JP); Tomohide Ida, Hino (JP); Yoshiyuki Sawai, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/258,173

(22) PCT Filed: Feb. 22, 2002

(86) PCT No.: PCT/JP02/01611
§ 371 (c)(1),
(2), (4) Date: Oct. 22, 2002

(87) PCT Pub. No.: WO02/066457
PCT Pub. Date: Aug. 29, 2002

(65) Prior Publication Data
US 2003/0176490 A1 Sep. 18, 2003

(30) Foreign Application Priority Data

Feb. 22, 2001 (JP) .................................. 2001-046275
May 7, 2001 (JP) .................................. 2001-135927

(51) Int. Cl.[7] .................... C07D 333/56; C07D 333/52; C07D 235/24
(52) U.S. Cl. .................... 549/58; 549/49; 548/306.4
(58) Field of Search .................. 549/58, 49; 548/306.4

(56) References Cited

U.S. PATENT DOCUMENTS

| 3,910,955 | A | | 10/1975 | Chapman et al. |
| 5,789,436 | A | * | 8/1998 | Kato et al. |
| 6,774,245 | B1 | * | 8/2004 | Saitoh et al. |

FOREIGN PATENT DOCUMENTS

| EP | 1 097 926 A1 | 5/2001 |
| EP | 1 249 450 A1 | 10/2002 |
| GB | 1 174 411 A | 12/1969 |
| JP | 20001 199968 A | 1/2000 |
| JP | 2001-199968 | 7/2001 |
| WO | WO 00/03997 | 1/2000 |
| WO | WO 01/53291 | 7/2001 |

OTHER PUBLICATIONS

Clark, Peter D. et al, CA89:42959, 1978.*
Tetrahedron, (1977), 33(24), p. 3233–8.
International Search Report.
Manuel Raga, et al; New Imidazole Antifungal Agent Derived From Benzo[b]thiophene; vol. 21, No. 4, 1986, pp. 329–332.
N.B. Chapman, et al; Synthesis of The Sulphur Analogue Of Psilocin and Some Related Compounds; Journal of the Chemical Society, Perkin Transactions 1: Organic and Bio–Organic Chemistry; No. 23, 1972, pp. 3011–3015.
M. Rosa Cuberes et al.; Halogeno–Substituted 2–and 3–Methylbenzo[b]thiophenes: Use of [1]H($^1$H) Nuclear Overhauser Effect for Locating the Halogen Substituent; Magnetic Resonance In Chemistry, vol. 23, No. 10. 1985, pp. 814–821.

(Continued)

Primary Examiner—Deborah C. Lambkin
(74) Attorney, Agent, or Firm—Sughrue Mion, PLLC

(57) ABSTRACT

The present invention is 3,4-disubstituted-benzo[b] thiophene derivatives represented by general formula (I) and processes for preparing compounds represented by general formula (V) from compounds represented by general formula (IV), preparing a mixture of compounds represented by the following formula (II) and the following formula (III) and preparing the benzo[b]thiophene derivatives represented by the above formula (I):

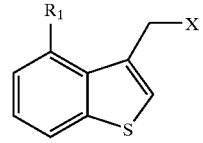

(I)

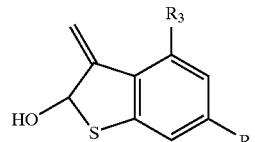

(IV)

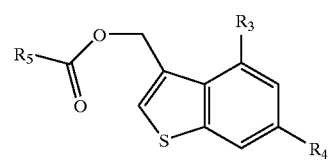

(V)

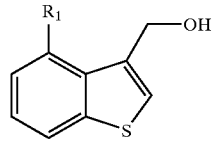

(II)

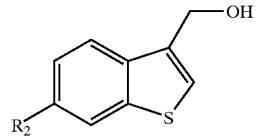

(III)

wherein, $R_1$ and $R_2$ represent each a halogen atom, a trihalomethyl group, a $C_{1-4}$ alkyl group or a $C_{1-4}$ alkoxy group; X represents a hydroxy group or a halogen atom; $R_3$ and $R_4$ represent each a hydrogen or a halogen atom, a trihalomethyl group, a $C_{1-4}$ alkyl group or a $C_{1-4}$ alkoxy group; and $R_5$ represents a $C_{1-3}$ alkyl group or a trifluoromethyl group.

20 Claims, No Drawings

OTHER PUBLICATIONS

Matthias K. Schwarz, et al; Solid–Phase Synthesis of 1,5–Benzodiazepin–2–ones; Tetrahedron Letter, Elsevier Science Publishers, Amsterdam, NL; vol. 39, No. 46. Nov. 12, 1998, pp. 8397–8400.

N.B. Chapman, et al; Pharmacologically Active Benzo[b] thiophen Derivative. Part VI.[1] 4–and 6–Halogeno–dervaties of N–2Chloroethyl–N–ethyl–3–aminomethyl–benzo[b] thiophen Hydrochloride; Journal of The Chemical Society, Section C:; vol. 22, 1968, pp. 2747–2751.

N.B. Chapman, et al.; Pharmacologically Active Benzo[b] thiophen Derivatives. Part IX. Some 4–and 5–Monosubstituted and 4,5–Disubstituted Amines and Thiouronium Salts; Journal Of The Chemical Society Section C Organic Chemistry, No. 5, 1971, pp. 915–919.

E. Campaigne et al; Benzo[b]thienylalanine and Derivaties [1], Journal Of Heterocyclic Chemistry; vol. 21, No. 4, 1984, pp. 1069–1071.

E. Champaigne, et al; Benzo[b]thiophene Derivaties. XXVI. 5–Methoxy–6–chloro–3–β–acetamidoethylbenzo[b] thiophene, A Blocked Analog of Melatonin (1), Journal Of Heterocyclic Chemistry, vol. 20, No. 1, 1983, pp. 55–59.

Phillippe Ohier, et al; Pyrrolo[1,4]diazepines, via Thermolyse of Carbonylazides, and [3,2,2] Cyclazines, via Diels–Alder Reaction of [f]Indolizines, Annelated to [1]Benzothiophene, Tetrahedron, vol., 52, No. 43, 1996, pp. 13547–13556.

N.B. Chapman, Some Reactions of 7–Chloro–3–methylbenzo[b]thiophen, Journal Of The Chemical Society, Perkin Transactions 1, 1972 pages 1404–1407.

N.B. Chapman et al., Synthesis of Some 5–Substituted Benzo[b]thiophens Related to Gramine, Journal Of The Chemical Society, 1965, pp. 774–777.

N.B. Chapman, et al, Pharmacologically Active Benzo[b] thiophen Derivaties. Part IV.+5–and 6–Alkyl Derivaties with an N–Alkyl–N–(2–chloroethyl) amino–methyl Group in the 3–Position, Journal Of The Chemical Society, 1968, pp. 514–517.

N.B. Chapman, et al, Pharmocologically Active benzo blthiophene hydrochlorides, Journal Of The Chemical Society, Section C, 1968 pp. 518–522.

Yasuo Makisumi et al, "Synthesis of condensed thiophenes via '2,31 And '3,31 Sigmatropic rearrangements of aryl prop–2–ynyl sulphoxides" Journal Of The Chemical Society. Chemical Communications, Chemical Society, Letchworth, GB, No. 20, 1974, pp. 848–849.

* cited by examiner

BENZO[B]THIOPHENE DERIVATIVES AND PROCESS FOR PREPARING THE SAME

TECHNICAL FIELD

The present invention relates to benzo[b]thiophene derivatives important as raw materials for preparing compounds useful in the pharmaceutical fields and processes for preparing the same.

BACKGROUND ART

Many substituted-benzo[b]thiophene derivatives have hitherto been synthesized and a plurality of the substituted-benzo[b]thiophene derivatives have been used as raw materials for chemicals, medicines and the like. Among them, 3-substituted-benzo[b]thiophene derivatives represented by the following formula (XIII):

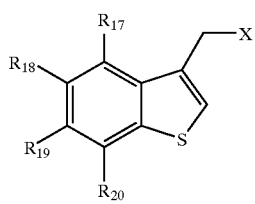

(XIII)

wherein, $R_{17}$ to $R_{20}$ represent simultaneously or each independently a hydrogen atom, a halogen atom, a trihalomethyl group, a $C_{1-4}$ alkyl group, a $C_{1-4}$ alkoxy group or a cyano group; and X represents a hydroxy group or a halogen atom, are exceedingly important as intermediates in preparing pharmacologically active compounds. For example, among the 3-substituted-benzo[b]thiophene derivatives represented by formula (XIII), compounds in which $R_{17}$ to $R_{20}$ represent each a hydrogen atom; and X represents a bromine atom, compounds in which $R_{17}$ represents a methyl group; $R_{18}$ to $R_{20}$ represent each a hydrogen atom; and X represents a bromine atom, compounds in which $R_{18}$ represents a methyl group; $R_{17}$, $R_{19}$ and $R_{20}$ represent each a hydrogen atom; and X represents a bromine atom and compounds in which $R_{17}$ and $R_{19}$ represent each a methyl group; $R_{18}$ and $R_{20}$ represent each a hydrogen atom; and X represents a bromine atom are capable of providing raw materials and the like for synthetic intermediates for benzimidazole derivatives as set forth in WO01/53291 and may be regarded as extremely important as intermediates in preparing pharmacologically active compounds. The benzimidazole derivatives as set forth in WO01/53291 are pharmaceutically useful benzimidazole derivatives and are considered to be promising as compounds applicable to prophylactic and/or therapeutic agents for various diseases including respiratory diseases such as bronchial asthma, sclerosing vascular lesions, intravascular stenosis and peripheral circulatory disorders.

Especially, because of structural features of 3,4-disubstituted-benzo[b]thiophene derivatives represented by the following formula (I):

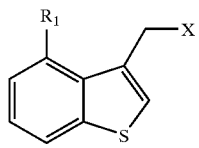

(I)

wherein, $R_1$ represents a halogen atom, a trihalomethyl group, a $C_{1-4}$ alkyl group or a $C_{1-4}$ alkoxy group; and X represents a hydroxy group or a halogen atom, isomers in the 4- and 6-positions thereof are produced when the benzo[b]thiophene skeleton is synthesized. Since the separation of the isomers is extremely difficult, no report has been made of the synthesis of the 3,4-disubstituted-benzo[b]thiophene derivatives. However, the 3,4-disubstituted-benzo[b]thiophene derivatives are remarkably expected as raw materials for highly active substances in development of medicines due to characteristic structures thereof.

Techniques described in "J. Chem. Soc., Chem. Comm., 848 (1974)" are cited as techniques related to synthesis of compounds of the present invention. The report has been made on reactions for introducing a propargyl group into benzenethiol, then carrying out oxidizing reaction, providing compounds represented by the following formula (XIV):

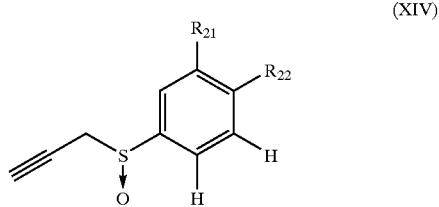

(XIV)

wherein, all of $R_{21}$ and $R_{22}$ are hydrogen atoms or a benzene ring may be formed of $R_{21}$ and $R_{22}$, then subjecting the resulting compounds represented by the formula (XIV) to thermal rearrangement reaction, affording compounds represented by the following formula (XV):

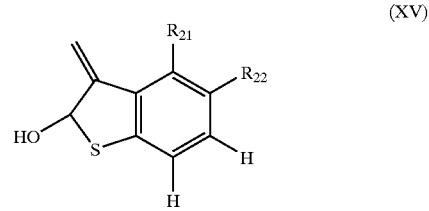

(XV)

wherein, all of $R_{21}$ and $R_{22}$ are hydrogen atoms or a benzene ring may be formed of $R_{21}$ and $R_{22}$, further subjecting the resulting compounds represented by the formula (XV) to thermal rearrangement reaction in the presence of p-toluenesulfonic acid in water-dioxane and providing compounds represented by the following formula (XVI):

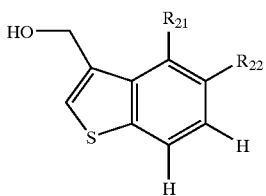

(XVI)

wherein, all of $R_{21}$ and $R_{22}$ are hydrogen atoms or a benzene ring may be formed of $R_{21}$ and $R_{22}$.

The reference, however, describes no 4-substituted-3-hydroxymethyl-benzo[b]thiophene derivative. As to the process for preparation, only conditions: in the presence of p-toluenesulfonic acid-dioxane are described.

When synthesis is carried out under the conditions described in the reference, by-products other than the 6-substituted-3-hydroxymethyl-benzo[b]thiophene derivatives which are isomers are produced in a higher proportion than that of the processes for preparation of the present invention. Thereby, the purification with column chromatography becomes essential and the synthesis under the conditions described in the reference is not suitable as an industrial process for preparation at all. In addition, a fraction of the objective substance obtained by column chromatography is a mixture of a 4-substituted-3-hydroxymethyl-benzo[b]thiophene and a 6-substituted-3-hydroxymethyl-benzo[b]thiophene in a ratio of about 3:2. The reference describes no method for separating the 4-substituted-3-hydroxymethyl-benzo[b]thiophene from the mixture. Complete separation cannot be carried out even by column chromatographic purification. The synthesis of the 4-substituted-3-hydroxymethyl-benzo[b]thiophene was very difficult according to the synthetic methods which have been reported up to present.

The yield of the 3-hydroxymethylbenzo[b]thiophene in the synthesis thereof in the reference is as low as 64% due to the synthesis of by-products, and the synthesis is industrially disadvantageous because steps are increased by taking the subsequent halogenation (synthesis of a 3-halomethyl-benzo[b]thiophene) and the like into consideration.

As other synthetic methods for the 3-halomethyl-benzo[b]thiophene derivatives, there are methods for reacting p-toluenethiol with bromoacetaldehyde diethyl acetal, providing a sulfide, then cyclizing the resulting sulfide with polyphosphoric acid, affording 5-methyl-benzo[b]thiophene, subsequently reacting the resulting 5-methyl-benzo[b]thiophene with hydrogen chloride gas-formaldehyde and introducing chloromethyl group [J. Chem. Soc., C, 514 (1968)] or methods for carrying out the Friedel-Crafts reaction of benzo[b]thiophene, synthesizing a 3-chloroacetyl-benzo[b]thiophene derivative to be a raw material [J. Chem. Soc., Perkin Trans. 2, 1250, (1973)], hydrolyzing the resulting 3-chloroacetyl-benzo[b]thiophene derivative and then reducing and halogenating the hydrolysis product and the like. In any of the methods, halomethyl groups are introduced into both the 2- and the 3-positions, and the selectivity thereof is not always high. Besides, the separation of the 3-halomethyl-benzothiophene derivatives from the 2-halomethyl-benzothiophene derivatives is extremely difficult.

From the above situation, the 4-substituted-3-hydroxymethyl-benzo[b]thiophene derivatives represented by formula (I) have been demanded and an efficient and simple synthetic method for the 4-substituted-3-hydroxymethyl-benzo[b]thiophene derivatives has been desired.

Furthermore, an efficient and simple synthetic method for the 3-halomethyl-benzo[b]thiophene derivatives has been desired.

DISCLOSURE OF THE INVENTION

It is an object of the present invention to provide 3,4-disubstituted-benzo[b]thiophene derivatives which have been difficult by conventional synthesis methods and to provide processes for preparing the same. It is another object of the present invention to provide processes for preparing high-purity 3-halomethyl-benzo[b]thiophene derivatives in short steps.

As a result of intensive studies made to achieve the above objects, the inventors have found out the 3,4-disubstituted-benzo[b]thiophene derivatives useful as raw materials for medicines and the like and have further found out selective synthetic methods for the 3,4-disubstituted-benzo[b]thiophene derivatives. In addition, the inventors have found out efficient synthetic methods for the 3-halomethyl-benzo[b]thiophene derivatives.

The present invention is 3,4-disubstituted-benzo[b]thiophene derivatives represented by formula (I):

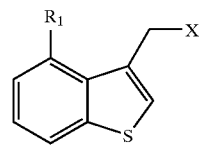

(I)

wherein, $R_1$ represents a halogen atom, a trihalomethyl group, a $C_{1-4}$ alkyl group or a $C_{1-4}$ alkoxy group; and X represents a hydroxy group or a halogen atom.

In the above formula (I), X represents preferably a hydroxy group, and $R_1$ represents more preferably a methyl group.

In the above formula (I), X represents preferably a halogen; and it is more preferable that $R_1$ represents a methyl group and X represents a bromine atom.

The present invention is a process for providing benzo[b]thiophene derivatives represented by the following formula (II):

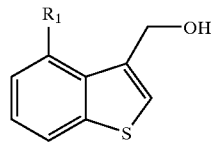

(II)

wherein, $R_1$ represents a halogen atom, a trihalomethyl group, a $C_{1-4}$ alkyl group or a $C_{1-4}$ alkoxy group, comprising crystallizing a mixture of the benzo[b]thiophene derivatives represented by the formula (II) and benzo[b]thiophene derivatives represented by the following formula (III):

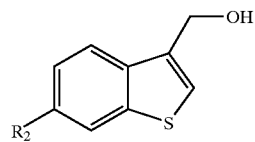

(III)

wherein, $R_2$ represents a halogen atom, a trihalomethyl group, a $C_{1-4}$ alkyl group or a $C_{1-4}$ alkoxy group, in a solvent. The solvent for crystallization is preferably a mixed solvent of a $C_{5-8}$ straight-chain, cyclic or branched hydrocarbon with a $C_{2-6}$ carboxylic acid ester, a mixed solvent of the $C_{5-8}$ straight-chain, cyclic or branched hydrocarbon with a $C_{6-8}$ aromatic hydrocarbon, or a solvent of acetonitrile.

Furthermore, the present invention is a process for preparing benzo[b]thiophene derivatives represented by the following formula (V):

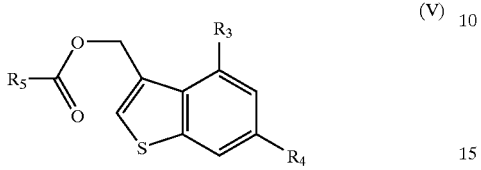
(V)

wherein, $R_3$ and $R_4$ are each the same as in the following formula (IV); $R_5$ represents a hydrogen atom, a $C_{1-3}$ alkyl group or a trifluoromethyl group, comprising reacting compounds represented by the following formula (IV):

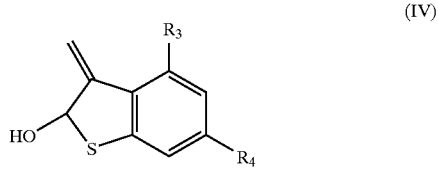
(IV)

wherein, $R_3$ represents a hydrogen and $R_4$ represents a halogen atom, a trihalomethyl group, a $C_{1-4}$ alkyl group or $C_{1-4}$ alkoxy group; or $R_3$ represents a halogen atom, a trihalomethyl group, a $C_{1-4}$ alkyl group or a $C_{1-4}$ alkoxy group; and $R_4$ represents a hydrogen, with one kind or two or more kinds of $C_{1-4}$ carboxylic acid anhydrides, trifluoroacetic acid, or its trifluoroacetic anhydride.

Further, the present invention is a process for preparing the benzo[b]thiophene derivatives represented by the above formula (II) or the benzo[b]thiophene derivatives represented by the above formula (III), namely a mixture comprising the compounds represented by formula (II) and formula (III), comprising reducing the compounds represented by the above formula (V) with a metal hydride complex compound or carrying out basic hydrolysis or acidic hydrolysis of the compounds represented by the above formula (V). The reduction is preferably conducted with sodium borohydride.

In addition, the present invention is a process for preparing the 4-substituted-3-hydroxymethyl-benzo[b]thiophene derivatives represented by the above formula (II) comprising:

introducing a propargyl group into m-substituted benzenethiols, providing compounds represented by the following formula (VI):

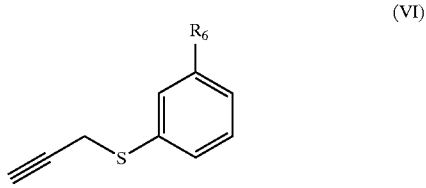
(VI)

wherein, $R_6$ represents a halogen atom, a trihalomethyl group, a $C_{1-4}$ alkyl group or a $C_{1-4}$ alkoxy group;

oxidizing the compounds represented by the above formula (VI), obtaining compounds represented by the following formula (VII):

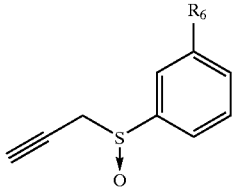
(VII)

wherein, $R_6$ represents the same as defined in the above formula (VI);

subjecting the compounds represented by the formula (VII) to thermal rearrangement reaction, providing the compounds represented by the above formula (IV);

reacting the obtained compounds represented by the formula (IV) with one kind or two or more kinds of $C_{1-4}$ carboxylic acids, their carboxylic acid anhydrides, trifluoroacetic acid, its trifluoroacetic anhydride, thereby obtaining the compounds represented by the above formula (V);

subsequently converting the ester group of the compounds represented by the formula (V) into a hydroxy group; and crystallizing the resulting mixture of the benzo[b]thiophene derivatives represented by the above formula (II) and the benzo[b]thiophene derivatives represented by the above formula (III) in a solvent. In the above formula (VI), $R_6$ represents preferably a methyl group.

Further, the present invention is a process for preparing 4-substituted-3-halomethyl-benzo[b]thiophene derivatives represented by the following formula (VIII):

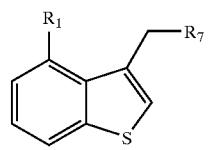
(VIII)

wherein, $R_1$ represents a halogen atom, a trihalomethyl group, a $C_{1-4}$ alkyl group or a $C_{1-4}$ alkoxy group; and $R_7$ represents a halogen atom, comprising further converting the hydroxy group of the 4-substituted-3-hydroxymethyl-benzo[b]thiophene derivatives represented by the above formula (II) into a halogen atom. In the above formula (VIII), $R_1$ is preferably a methyl group.

In addition, the present invention is a process for preparing 3-halomethyl-benzo[b]thiophene derivative compounds represented by the following formula (X):

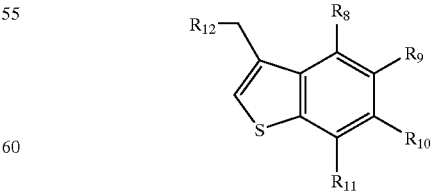
(X)

wherein, $R_8$ to $R_{11}$ are each the same as in the general formula (IX); $R_{12}$ represents a halogen atom, comprising reacting compounds represented by the following formula (IX):

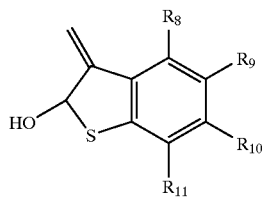

(IX)

wherein, $R_8$ to $R_{11}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group, with an equivalent amount or more of an acid.

Furthermore, the present invention is a process for preparing the compounds represented by the formula (X) comprising: introducing a propargyl group into substituted benzenethiols, providing compounds represented by the following formula (XI):

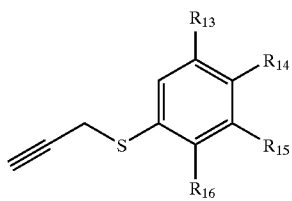

(XI)

wherein, $R_{13}$ and $R_{15}$ represent simultaneously and $R_{14}$ represents independently a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group; and $R_{16}$ represents a hydrogen atom: or $R_{16}$ represents a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group or a trihalomethoxy group; and $R_{13}$ to $R_{15}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group;

oxidizing the resulting compounds represented by formula (XI), providing compounds represented by the following formula (XII):

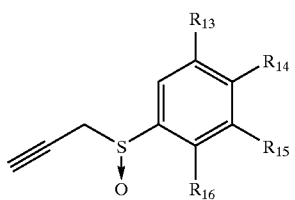

(XII)

wherein, $R_{13}$ to $R_{16}$ are each the same as in the above formula (XI);

subjecting the compounds represented by the formula (XII) to thermal rearrangement reaction, obtaining the compounds represented by the above formula (IX); and reacting the resulting compounds represented by the above formula (IX) with an equivalent amount or more of an acid.

It is preferable that, in the above formula (IX) and the above formula (X), $R_8$ and $R_{10}$ represent simultaneously and $R_9$ represents independently a hydrogen atom or a $C_{1-4}$ alkyl group, and $R_{11}$ represents a hydrogen atom; or $R_{11}$ represents a $C_{1-4}$ alkyl group, and $R_8$ to $R_{10}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group or a trihalomethoxy group: and $R_{13}$ and $R_{15}$ in the above formula (XI) and the above formula (XII) represent simultaneously and $R_{14}$ represents independently a hydrogen atom or a $C_{1-4}$ alkyl group, and $R_{16}$ represents a hydrogen atom; or $R_{16}$ represents a $C_{1-4}$ alkyl group, and $R_{13}$ to $R_{15}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group or a trihalomethoxy group.

In the above formula (X) of the present invention, $R_{12}$ is preferably a chlorine atom or a bromine atom.

Further, the present invention is a process for preparing benzimidazole derivatives represented by the general formula (XX):

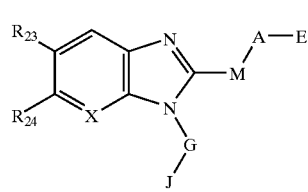

(XX)

in the formula (XX), $R_{23}$ and $R_{24}$ represent simultaneously or each independently a hydrogen atom, a halogen atom, a trihalomethyl group, a cyano group, a hydroxy group, a $C_{1-4}$ alkyl group or a $C_{1-4}$ alkoxy group; or $R_{23}$ and $R_{24}$ together represent —O—CH$_2$O—, —O—CH$_2$CH$_2$—O— or —CH$_2$CH$_2$CH$_2$— (in this case, the each carbon atom may be substituted with one or plural $C_1$-$C_4$ alkyl groups);

A represents a substituted or an unsubstituted $C_1$-$C_7$ straight-chain, cyclic or branched alkylene group or alkenylene group which may be interrupted by one or more of —O—, —S—, —SO$_2$— and —NR$_{25}$— (wherein, $R_{25}$ represents a hydrogen atom or a straight-chain or a branched $C_{1-6}$ alkyl group); the substituents which can be possessed by the groups are each a halogen atom, a hydroxy group, a nitro group, a cyano group, a straight-chain or a branched $C_{1-6}$ alkyl group, a straight-chain or a branched $C_{1-6}$ alkoxy group (including the case where two adjacent groups form an acetal bond, namely including the case in which the alkyl portious of geminal two alkoxy groups are connected to form a ring), a straight-chain or a branched $C_{1-6}$ alkylthio group, a straight-chain or a branched $C_{1-6}$ alkylsulfonyl group, a straight-chain or a branched $C_{1-6}$ acyl group, a straight-chain or a branched $C_{1-6}$ acylamino group, a trihalomethyl group, a trihalomethoxy group, a phenyl group, an oxo group, or a phenoxy group which may be substituted with one or more halogen atoms; the one or plural substituents may independently be substituted at optional positions of the alkylene group or alkenylene group except that hydroxy group and phenyl group are simultaneously substituted at the carbon of A which is bound to M that be a single bond in the formula (XX);

E represents a —COOR$_{25}$, a —SO$_3$R$_{25}$, a CONHR$_{25}$, a —SO$_2$NHR$_{25}$, a tetrazol-5-yl group, a 5-oxo-1,2,4-oxadiazol-3-yl group or a 5-oxo-1,2,4-thiadiazol-3-yl group (where $R_{25}$ is as defined above);

M represents a single bond or —S(O)$_m$—; where m is an integer of 0 to 2;

G and J represent each the above formula (I) or the above formula (X), with the proviso that G represents a methylene group in the 3-position of the benzothiophene represented by the above formula (I) and the above formula (X), and X of the above formula (I) and R$_{12}$ of the above formula (X) are each replaced with nitrogen atom on the benzimidazole ring; and X represents —CH= or nitrogen atom, from the compounds represented by the above formula (I) or the above formula (X).

MODE FOR CARRYING OUT THE INVENTION

Examples of the benzothiophene derivatives and processes for preparing the same according to the present invention will be cited hereinafter. The present invention, however, is not limited by the examples.

Examples of the 3,4-disubstituted-benzo[b]thiophene derivatives and processes for preparing the same are initially cited hereunder.

The present invention is the 3,4-disubstituted-benzo[b] thiophene derivatives represented by formula (I):

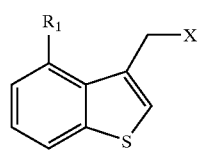
(I)

wherein, R$_1$ represents a halogen atom, a trihalomethyl group, a C$_{1-4}$ alkyl group or a C$_{1-4}$ alkoxy group; and X represents a hydroxy group or a halogen atom. Preferable examples of R$_1$ include a trihalomethyl group and a methyl group. More preferable examples include a methyl group. Preferable examples of X include a hydroxy group, a bromine atom and a chlorine atom.

Specifically, compounds listed in Table 1 are preferable as the compounds represented by formula (I). Compound Nos. 1, 2 and 3 are especially preferable compounds in the table.

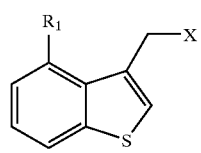
(I)

TABLE 1

| Compound No. | R$_1$ | X |
|---|---|---|
| 1 | Me | OH |
| 2 | Me | Cl |
| 3 | Me | Br |
| 4 | CF$_3$ | OH |
| 5 | CF$_3$ | Cl |
| 6 | CF$_3$ | Br |

(Me represents a methyl group).

As a process for preparing the compounds represented by formula (I), compounds represented by formula (IV):

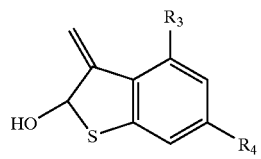
(IV)

wherein, R$_3$ represents a hydrogen and R$_4$ represents a halogen atom, a trihalomethyl group, a C$_{1-4}$ alkyl group or a C$_{1-4}$ alkoxy group; or R$_3$ represents a halogen atom, a trihalomethyl group, a C$_{1-4}$ alkyl group or C$_{1-4}$ alkoxy group, and R$_4$ represents a hydrogen, are reacted with one kind or two or more kinds selected from the group consisting of C$_{1-4}$ carboxylic acids, trifluoroacetic acid, carboxylic acid anhydrides and trifluoroacetic anhydride to thereby prepare compounds represented by formula (V):

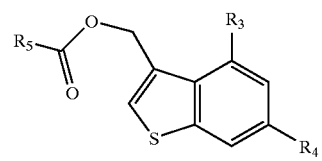
(V)

wherein, R$_3$ and R$_4$ are each the same as defined in formula (IV); R$_5$ represents a hydrogen atom, a C$_{1-3}$ alkyl group or a trifluoromethyl group.

In the present invention, examples of a solvent used for reaction from formula (IV) to formula (V) include toluene, tetrahydrofuran, dioxane, i-propyl acetate or n-propyl acetate. Preferable examples include toluene, tetrahydrofuran and dioxane.

Examples of the carboxylic acids or acid anhydrides include acetic acid, trifluoroacetic acid, acetic anhydride and trifluoroacetic anhydride. Preferable examples include trifluoroacetic acid and trifluoroacetic anhydride. More preferable examples include trifluoroacetic anhydride.

The ester group of the compounds represented by formula (V) is then converted into a hydroxy group to thereby obtain a mixture comprising the compounds represented by formula (II) and formula (III). The ester group of the compounds represented by formula (V) is converted into the hydroxy group of the compounds represented by formula (II) by acid hydrolysis, basic hydrolysis, reduction with a metal hydride complex compound or the like, preferably by basic hydrolysis or reduction with a metal hydride complex compound. Lithium hydroxide, sodium hydroxide or the like are preferable as a base for the basic hydrolysis. Lithium aluminum hydride, sodium borohydride or the like are cited as the metal hydride complex compound, and sodium borohydride is preferable.

The 4-substituted-3-hydroxymethyl-benzo[b]thiophene derivatives represented by formula (II) is obtained by crystallizing a mixture comprising the compounds represented by formula (II) and formula (III) in a solvent. A solvent for crystallization is not especially limited, however, it is preferable to crystallize in a mixed solvent of a C$_{5-8}$ straight-chain, cyclic or branched hydrocarbon and a C$_{2-6}$ carboxylic acid ester, a mixed solvent of the C$_{5-8}$ straight-chain, cyclic or branched hydrocarbon and a C$_{6-8}$ aromatic hydrocarbon, or in acetonitrile.

Preferable examples of the hydrocarbon include pentane, hexane, cyclohexane, heptane and octane. More preferable examples include hexane and cyclohexane. The hydrocarbon may be used as a single solvent or a mixed solvent. Preferable examples of the aromatic hydrocarbon include benzene, toluene and xylene. More preferable examples of aromatic hydrocarbon include toluene. Preferable examples of the carboxylic acid of the carboxylic acid ester include formic acid, acetic acid and propionic acid. Preferable examples of the ester include a methyl ester, an ethyl ester, a propyl ester, an isopropyl ester. Preferable examples of the carboxylic acid ester include methyl acetate, ethyl acetate, propyl acetate, isopropyl acetate, ethyl formate and ethyl propionate. More preferable example is Ethyl acetate.

A combination of solvents of preferable crystallization conditions include hexane-ethyl acetate, cyclohexane-ethyl acetate, hexane-cyclohexane-ethyl acetate, hexane-toluene, cyclohexane-toluene, hexane-cyclohexane-toluene, hexane-xylene, cyclohexane-xylene, and hexane-cyclohexane-xylene, or a solvent of preferable crystallization conditions is acetonitrile.

As conditions of crystallization, there can be cited methods for refluxing the mixture in a mixed solvent of a $C_{5-8}$ straight-chain, cyclic or branched hydrocarbon and $C_{2-6}$ carboxylic acid ester, in a mixed solvent of a $C_{5-8}$ straight-chain, cyclic or branched hydrocarbon and a $C_{6-8}$ aromatic hydrocarbon, or in acetonitrile, then cooling, and carrying out crystallization; or methods for dissolving the mixture in a $C_{6-8}$ aromatic hydrocarbon or a $C_{2-6}$ carboxylic acid ester, and then adding a $C_{5-8}$ straight-chain, cyclic or branched hydrocarbon, and thereby carrying out crystallization in the mixed solvent.

Ratios of the mixed solvent are the $C_{5-8}$ hydrocarbon:carboxylic acid ester=1:2 to 9:1. Preferable ratios are the $C_{5-8}$ hydrocarbon:carboxylic acid ester=1:2 to 5:1. Ratios when a $C_{6-8}$ aromatic hydrocarbon is used are the $C_{5-8}$ hydrocarbon:aromatic hydrocarbon=1:2 to 5:1. Preferable ratios are the $C_{5-8}$ hydrocarbon:aromatic hydrocarbon=1:2 to 3:1. Examples of preferable crystallizing conditions are a ratio of hexane:ethyl acetate=1:2 to 5:1, a ratio of a mixed solvent of cyclohexane and hexane:ethyl acetate=1:2 to 5:1, a ratio of hexane:toluene=1:2 to 3:1, and a ratio of a mixed solvent of cyclohexane and hexane:toluene=1:2 to 3:1. A preferable ratio of cyclohexane to the hexane is cyclohexane:hexane=1:3 to 3:1.

The amount of the solvent based on a substrate is not especially limited, however, preferable amount are 1 to 10 times based on the substrate weight, more preferable amount are 2 to 5 times based on the substrate weight.

The hydroxy group of the resulting compounds represented by formula (II), if necessary, can be converted into a halogen atom to obtain the 4-substituted-3-halomethyl-benzo[b]thiophene derivative represented by formula (VIII).

Examples of reagent for halomethylation from formula (II) to formula (VIII) of the present invention are a hydrogen halide, a phosphorus halide, a sulfonyl chloride, a thionyl halide and the like. Preferable examples of reagent are a phosphorus halide and a thionyl halide. A more preferable examples of reagent is phosphorus tribromide.

A method for synthesizing the compounds represented by formula (II) of the present invention from a commercially available raw material compound will be explained hereinafter. The method can suitably be selected, however, it is preferable that synthesis can efficiently be carried out in high purity by the method as set forth in the following. The method is explained by citing specific examples hereunder:

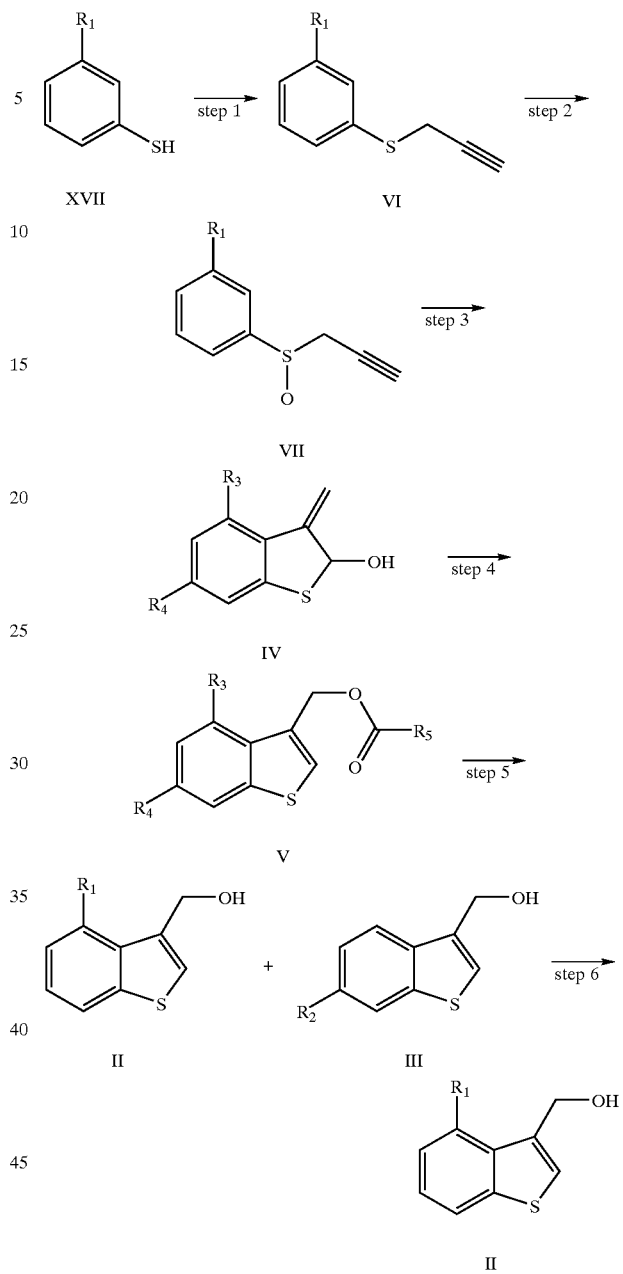

(First Step)

The compounds represented by formula (VI) is obtained by introducing a propargyl group into the mercapto group of m-toluenethiols represented by formula (XVII).

The introduction of the propargyl group is carried out in the presence of a basic substance, by using a propargyl halide, for example propargyl bromide or propargyl chloride. As the basic substance, for example, examples of an inorganic base include potassium carbonate and sodium carbonate, and examples of an organic base include triethylamine, pyridine and 4-dimethylaminopyridine. Examples of a solvent include toluene, acetone, ethyl acetate, tetrahydrofuran, acetonitrile and 2-butanone. Preferable examples of a solvent include toluene and 2-butanone. The reaction can be completed at room temperature to the refluxing temperature, for several tens of minutes to several hours.

(Second Step)

The compounds represented by formula (VII) is obtained by oxidation of the compounds represented by formula (VI). The oxidizing reaction of sulfur atom is carried out by using an oxidizing agent, for example potassium persulfate, aqueous hydrogen peroxide, metaperiodates, perchlorates or m-chloroperbenzoic acid, with an appropriate solvent, for example an aromatic hydrocarbon such as toluene or xylene, alcohols, acetone or water alone or in combination. Preferable example of this step is a method for stirring 1 to 1.2 equivalents of sodium metaperiodate, into the compounds represented by formula VI, in a solvent of an alcohol-water such as methanol, ethanol or isopropanol, at room temperature, for several tens of minutes to several hours.

(Third Step)

The compounds represented by formula (IV) is obtained by cyclizing rearrangement of the sulfoxide of formula (VII).

In the case of the sulfoxide used in the present invention, preferable solvents include dioxane, propyl acetate, toluene, and xylene. More preferable solvents are dioxane and toluene. A still more preferable example is toluene. The amount of the solvent is preferably 10 times or more based on the substrate weight, more preferably 15 to 30 times based on the substrate weight.

The reaction temperature is preferably 60° C. or above, especially preferably 80 to 100° C.

In this step, the reaction of the compounds represented by formula (VII) proceeds even by heating after dissolving in the solvent, however, it is a preferable method for preheating the solvent to the reaction temperature and dropping a solution of the compounds represented by formula (VII) to the solvent.

The heating time is not especially limited; however, the heating time after dropping the substrate at the reaction temperature is preferably kept for several tens of minutes to 2 hours, especially preferably within 1 hour from the completion of the dropping the substrate.

By carrying out the reaction under the conditions, the formation of by-products can extremely be suppressed, and the yield can be improved.

(Fourth Step)

This step is a step of reacting cyclized substances [formula (IV)] obtained in the third step with a carboxylic acid or a carboxylic acid anhydride, and obtaining the compounds represented by formula (V).

In this step, esterifying rearrangement reaction proceeds by adding the carboxylic acid or the carboxylic acid anhydride to the reaction system without concentrating the reaction solvent used in the third step. Similar reaction proceeds even by concentrating the solvent in the third step and carrying out the reaction in another solvent. Trifluoroacetic acid is preferred as the carboxylic acid of this step, and trifluoroacetic anhydride is preferred as the carboxylic acid anhydride. The amount of the carboxylic acid or carboxylic acid anhydride is preferably 0.5 to 1.2 equivalents to the substrate, and especially preferably 0.5 to 0.8 equivalent is preferably dropped into a substrate solution The reaction temperature during the dropping of the carboxylic acid or carboxylic acid anhydride in the reaction of this step is preferably 0 to 50° C., more preferably 20 to 30° C.

The reaction of this step is completed in several minutes to several hours when the reaction is carried out at room temperature.

(Fifth Step)

This step is a step of obtaining the compounds represented by formula (II) or formula (III) by hydroxylation of the ester derivatives represented by formula (V) obtained in the fourth step.

Basic hydrolysis, or reduction with the metal hydride complex compound is preferable as the conditions. The base for the basic hydrolysis is not especially limited, however, preferable examples are lithium hydroxide and sodium hydroxide. The solvent for hydrolysis is not especially limited, however, a tetrahydrofuran-water system is preferable. In the case of the reduction with the metal hydride complex compound, examples of the metal hydride complex compound are lithium aluminum hydride, sodium borohydride, sodium cyanotrihydroborate and the like. Preferable example is the sodium borohydride. The amount of the base for the basic hydrolysis or metal hydride complex compound is preferably 0.5 to 1 equivalent of the substrate.

The solvent of the reaction system is not especially limited, however, preferable examples are tetrahydrofuran and toluene.

(Sixth Step)

This step is a step of separating the each compound represented by formula (II) and formula (III) from a mixture of the 4-substituted-3-hydroxymethyl-benzo[b]thiophene derivatives represented by formula (II) and the 6-substituted-3-hydroxymethyl-benzo[b]thiophene derivatives represented by formula (III).

Preferable examples of solvent for crystallization in this step are hexane-ethylacetate, a cyclohexane-ethyl acetate and a hexane-toluene system. Examples of preferable crystallizing conditions are hexane:ethyl acetate=1:2 to 5:1, a mixed solvent of cyclohexane and hexane:ethyl acetate=1:2 to 5:1, hexane:toluene=1:2 to 3:1, a mixed solvent of cyclohexane and hexane:toluene=1:2 to 3:1 and the like. Further, preferable ratio of the cyclohexane to the hexane are cyclohexane:hexane=1:3 to 3:1.

The amount of the solvent based on the substrate is not especially limited, however, it is preferable that an amount is 1 to 10 times based on the substrate weight; it is more preferable that an amount is 2 to 5 times based on the substrate.

The compounds represented by formula (II) can be separated from the mixture of the compounds represented by formula (II) and formula (III), by crystallization according to this step.

(Seventh Step)

Although a synthetic method for the compounds represented by formula (VIII) from the compounds represented by formula (II) is not especially limited; however, the following method is more preferable:

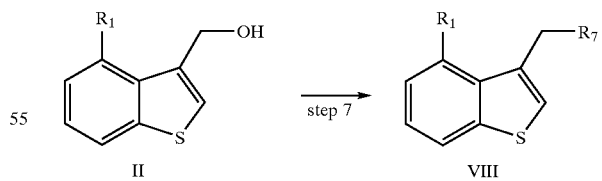

This step is a step of replacing the hydroxyl group of the 4-substituted-3-hydroxymethyl-benzo[b]thiophene derivatives with a halogen atom.

Examples of reagent for halomethylation of halogen replacement are a hydrogen halide, a phosphorus halide, sulfonyl chloride, a thionyl halide and the like. Preferable examples are the phosphorus halide or thionyl halide. More preferable example is phosphorus tribromide.

A hydrocarbon such as cyclohexane or hexane, or an aromatic hydrocarbon such as benzene, toluene or xylene is cited as the solvent. Cyclohexane or toluene can preferably be cited. The reaction can be completed at room temperature to the refluxing temperature, for several tens of minutes to several hours. After the reaction, the compounds represented by formula (VIII), if necessary, may be crystallized. Example of the solvent for crystallization is a hydrocarbon such as heptane, hexane or cyclohexane. Preferable examples are cyclohexane and heptane.

The synthetic method for the 3-halomethyl-benzo[b]thiophene derivatives will be detailed hereinafter.

The present invention is a process for preparing the 3-halomethyl-benzo[b]thiophene derivatives represented by formula (X):

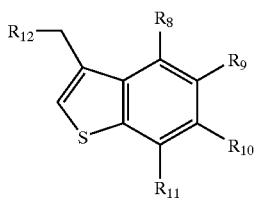

(X)

wherein, $R_8$ to $R_{11}$ are each the same as in the following formula (IX); and $R_{12}$ represents a halogen atom, comprising reacting compounds represented by formula (IX):

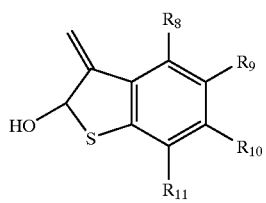

(IX)

wherein, $R_8$ to $R_{11}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group or a trihalomethoxy group, with an equivalent amount or more of an acid.

Preferable examples of $R_8$ to $R_{11}$ in the present invention are a hydrogen atom and a $C_{1-4}$ alkyl group.

The positions of the hydrogen atoms or alkyl groups of $R_8$ to $R_{11}$ are simultaneously or each independently optional, however, it is preferable the case where all are hydrogen atoms, $R_8$, $R_{10}$ and $R_{11}$ are each a hydrogen atom and $R_9$ is a $C_{1-4}$ alkyl group, and $R_9$ and $R_{11}$ are each a hydrogen atom and $R_8$ and $R_{10}$ are each a $C_{1-4}$ alkyl group.

Compounds listed in Table 2 are preferable as the compound represented by formula (X). In the Table, especially preferable compounds are compound Nos. 7, 8 and 9.

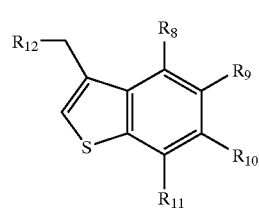

(X)

TABLE 2

| Compound No. | $R_8$ | $R_9$ | $R_{10}$ | $R_{11}$ | $R_{12}$ |
|---|---|---|---|---|---|
| 7 | H | H | H | H | Br |
| 8 | H | Me | H | H | Br |
| 9 | Me | H | Me | H | Br |
| 10 | H | H | H | H | Cl |
| 11 | H | Me | H | H | Cl |
| 12 | Me | H | Me | H | Cl |

(Me represents a methyl group).

In the present invention, examples of an acid used for reaction from formula (IX) to formula (X) are hydrogen chloride gas, hydrogen bromide gas, a hydrogen chloride-dioxane solution, hydrochloric acid, hydrobromic acid, hydroiodic acid and the like. Preferable examples are the hydrogen chloride-dioxane solution and hydrobromic acid. It is necessary to add the acid in an equivalent amount or more of the substrate, however, the amount is preferably 1.2 to 3 equivalents, more preferably 1.2 to 1.5 equivalents.

The solvent of the present invention is not especially limited, however, preferable examples are dioxane, propyl acetate and toluene. The amount of the solvent is 5 times or more based on the substrate weight, preferably 10 to 20 times based on the substrate weight.

In the present invention, the reaction is carried out at a reaction temperature of preferably 0 to 50° C., especially preferably 0 to 30° C.

The synthetic method for the compounds represented by formula (IX) is not especially limited; however, the following method is preferable.

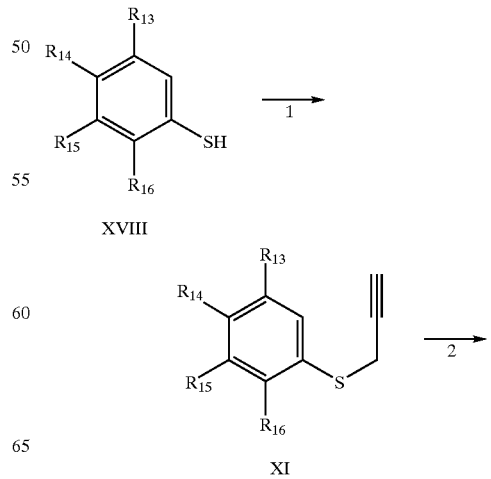

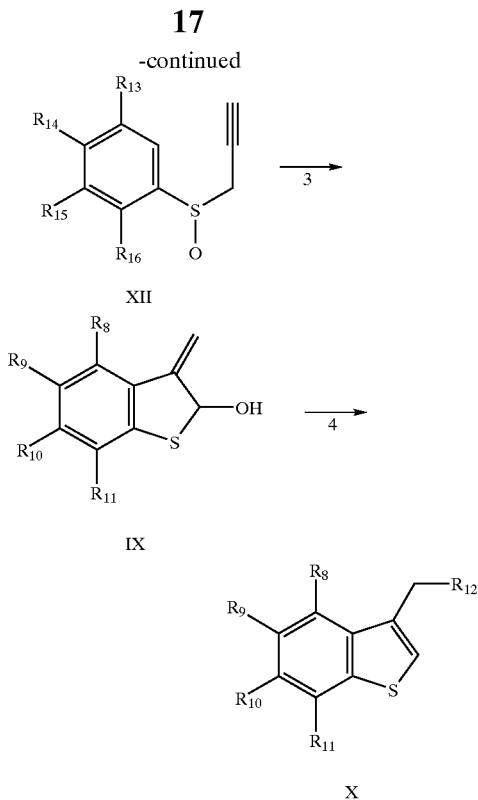

(First Step)

This step is a step of introducing a propargyl group into the mercapto group of the substituted benzenethiols represented by formula (XVIII), and obtaining the compounds represented by formula (XI).

The introduction of the propargyl group is carried out in the presence of a basic substance, using a propargyl halide, for example propargyl bromide or propargyl chloride. As the basic substance, for example, potassium carbonate or sodium carbonate is used as an inorganic base, and triethylamine, pyridine or 4-dimethylaminopyridine is used as an organic base. The introduction of the propargyl group can be carried out in a solvent such as acetone, ethyl acetate, tetrahydrofuran, acetonitrile, 2-butanone, toluene or the like, at room temperature to the refluxing temperature in several hours.

(Second Step)

This step is a step of preparing the compounds represented by formula (XII) by oxidizing the compounds represented by formula (XI). In this step, a method for stirring the compounds represented by formula (XII) with 1.2 equivalents of sodium metaperiodate in an alcohol-water solvent system such as methanol, ethanol, isopropanol or the like at room temperature is preferable. The reaction is completed under the above conditions in several hours.

(Third Step)

This step is a step of obtaining the compounds represented by formula (IX) by cyclizing rearrangement of the sulfoxide of the compounds represented by formula (XII). The method described in J. C. S. Chem. Comm., 848–849, 1974 is helpful in the thermal rearrangement reaction of this step.

In the case of the reaction of the sulfoxide used in the present invention, dioxane, propyl acetate, toluene, xylene or the like is cited as a preferable solvent. The amount of the solvent is not especially limited; however, the amount is preferably 10 times or more based on the substrate weight, more preferably 15 times to 30 times based on the substrate weight. By carrying out the reaction with the amount of the solvent, the formation of by-products can extremely be suppressed and the yield can be improved. The reaction temperature is not especially limited; however, the reaction is carried out at a temperature of preferably 80° C. or above, more preferably 100° C. to the refluxing temperature of the solvent.

The reaction is achieved in several tens of minutes to several hours when the reaction is carried out at the refluxing temperature.

(Fourth Step)

This step is a step of further reacting cyclized substances of the compounds represented by formula (IX) obtained in the third step with an acid, and preparing the compounds represented by formula (X).

As for the solvent in this step, halomethylating rearrangement reaction proceeds by adding an acid to the reaction system without concentrating the reaction solvent used in the third step. Similar reaction proceeds even when the solvent in the third step is concentrated and the reaction is carried out in another solvent. Preferable examples of the acid in this reaction are hydrogen chloride gas, hydrogen bromide gas, hydrochloric acid, hydrobromic acid, hydroiodic acid, a hydrogen chloride-dioxane solution and the like. The reaction temperature in this reaction is preferably 0 to 50° C., preferably 0 to 30° C. The reaction is achieved in about several tens of minutes to several hours.

By using the benzothiophene derivatives represented by formula (X) prepared by the method mentioned above, pharmaceutically useful benzimidazole derivatives can be synthesized according to the method described in, for example WO01/53291.

The pharmacologically active and useful benzimidazole derivatives [general formula (XX)] can be obtained by using the 3-substituted-benzo[b]thiophene derivatives represented by formula (XIII) or formula (I) as an intermediate:

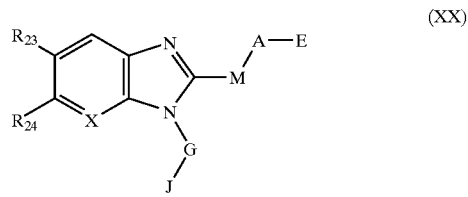

in the formula (XX), $R_{23}$ and $R_{24}$ represent simultaneously or each independently a hydrogen atom, a halogen atom, a trihalomethyl group, a cyano group, a hydroxy group, a $C_{1-4}$ alkyl group or a $C_{1-4}$ alkoxy group; or $R_{23}$ and $R_{24}$ together represent —O—$CH_2$—O—, —O—$CH_2CH_2$—O—, or —$CH_2CH_2CH_2$— (in this case, each the carbon atom may be substituted with one or plural $C_{1-4}$ alkyl groups);

A is a substituted or an unsubstituted $C_{1-7}$ straight-chain, cyclic or branched alkylene group or alkenylene group which may be interrupted by more of —O—, —S—, —$SO_2$— and —$NR_{25}$— (wherein $R_{25}$ is a hydrogen atom or a straight-chain or branched chain $C_{1-6}$ alkyl group); the substituents which can be possessed by the groups are each a halogen atom, a hydroxy group, a nitro group, a cyano group, a straight-chain or a branched $C_{1-6}$ alkyl group, a straight-chain or a branched $C_{1-6}$ alkoxy group (including the case in which two adjacent groups form an acetal bond), a straight-chain or a branched $C_{1-6}$ alkylthio group, a straight-chain or a branched $C_{1-6}$ alkylsulfonyl group, a straight-chain or a branched $C_{1-6}$ acyl group, a straight-chain or a branched $C_{1-6}$ acylamino group, a trihalomethyl group, a trihalomethoxy group, a phenyl group, an oxo group or a phenoxy group which may be substituted with one or more halogen atoms; the one or more of these substituents may independently be substituted in optional sites of the alkylene group or alkenylene group, except that hydroxy group and phenyl group are simultaneously substituted at the carbon atom of A bound to M, and M is with a single bond in the formula (XX);

E represents —COOR$_{25}$, —SO$_3$R$_{25}$, —CONHR$_{25}$, —SO$_2$NHR$_{25}$, tetrazol-5-yl group, 5-oxo-1,2,4-oxadiazol-3-yl group or 5-oxo-1,2,4-thiadiazol-3-yl group (wherein, R$_{25}$ represents the same as in described above);.

M represents a single bond or —S(O)$_m$—; m is an integer of 0 to 2;

G and J represent each the formula (I) or (X), with the proviso that G represents methylene group in the 3-position of the benzothiophene represented by the above formula (I) and the above formula (X), and X of the above formula (I) and R$_{12}$ of the above formula (X) represent each a nitrogen atom on the benzimidazole ring: and X represents —CH= or a nitrogen atom.

The benzimidazole derivatives (XX) can be prepared by a synthetic method (A) or a synthetic method (B), when E is COOR$_{25}$ and M is S.

Synthetic method (A)

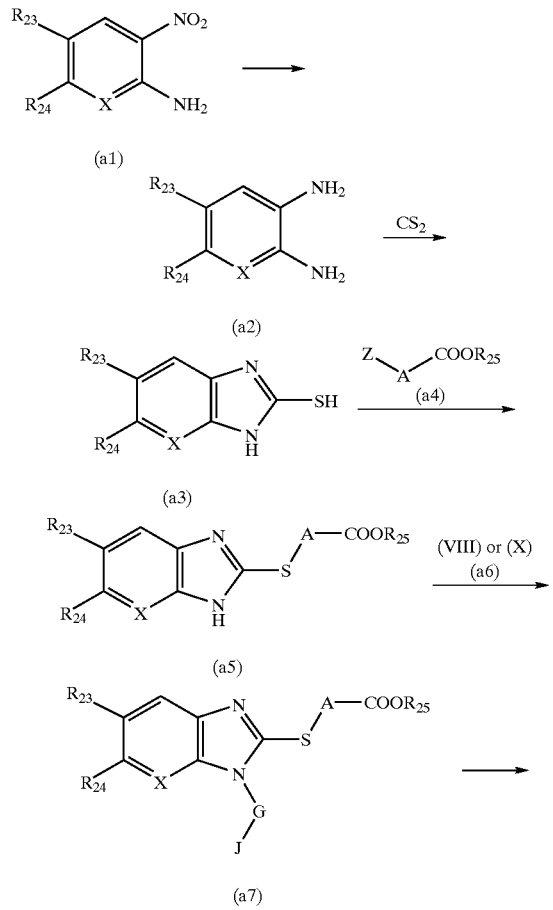

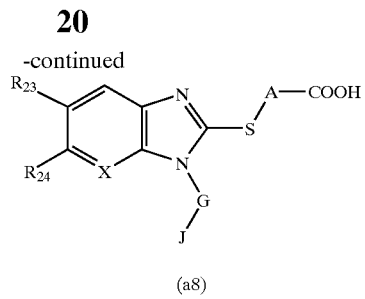

(a8)

wherein, Z represents a halogen or an ammonium salt; R$_{23}$, R$_{24}$, R$_{25}$, A, G, J and X are each the same as defined above.

Namely, the nitro group of the 2-nitroaniline derivative (a1) is reduced to obtain an o-phenylenediamine (a2), then the o-phenylenediamine (a2) is reacted with CS$_2$ to afford a compound (a3). The resulting compound (a3) is subsequently reacted with a halide ester derivative (a4) to obtain a compound (a5), then the compound (a5) is reacted with a halide derivative (a6) represented by the above formula (VIII) or the above formula (X). Thereby, a compound (a7) can be obtained. The resulting compound (a7), if necessary, can be hydrolyzed to obtain a benzimidazole derivative (a8) in which R$_{25}$ is a hydrogen atom.

The reduction of the nitro group can be carried out, in accordance with the conditions of an ordinary catalytic reduction, by reacting the nitro group with hydrogen gas at a temperature of room temperature to 100° C. in the presence of a catalyst, for example Pd-C under acidic, neutral or alkaline conditions. The reduction can be conducted by a method for treatment using zinc or tin under acidic conditions or a method for using zinc dust under neutral or alkaline conditions.

The reaction of the o-phenylenediamine derivative (a2) with CS$_2$ can be carried out by a method described in, for example, the Journal of Organic Chemistry (J. Org. Chem.), 1954, Vol. 19, pp. 631–637 (a pyridine solution) or the Journal of Medicinal Chemistry (J. Med. Chem.), 1993, Vol. 36, pp. 1175–1187 (an ethanol solution).

The reaction of thiobenzimidazoles (a3) with the halide ester derivative (a4) can be conducted by stirring in the presence of a base, such as NaH, Et$_3$N, NaOH or K$_2$CO$_3$ at a temperature of 0 to 200° C. in accordance with the conditions of an ordinary S-alkylation reaction.

The reaction of the thiobenzimidazoles (a5) with the halide derivative or an ammonium salt (a6) can be carried out by stirring in the presence of a base, for example, NaH, Et$_3$N, NaOH, K$_2$CO$_3$ or Cs$_2$CO$_3$ at a temperature of 0 to 200° C. according to usual N-alkylating or N-acylating reaction conditions.

A method for hydrolysis using an alkali such as lithium hydroxide or an acid such as hydrochloric acid or trifluoroacetic acid is preferably used for eliminating reaction of the protecting group R$_{25}$ of the carboxy group.

Synthetic method (B)

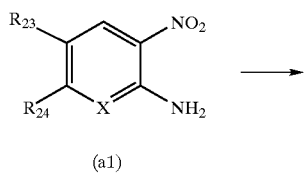

(a1)

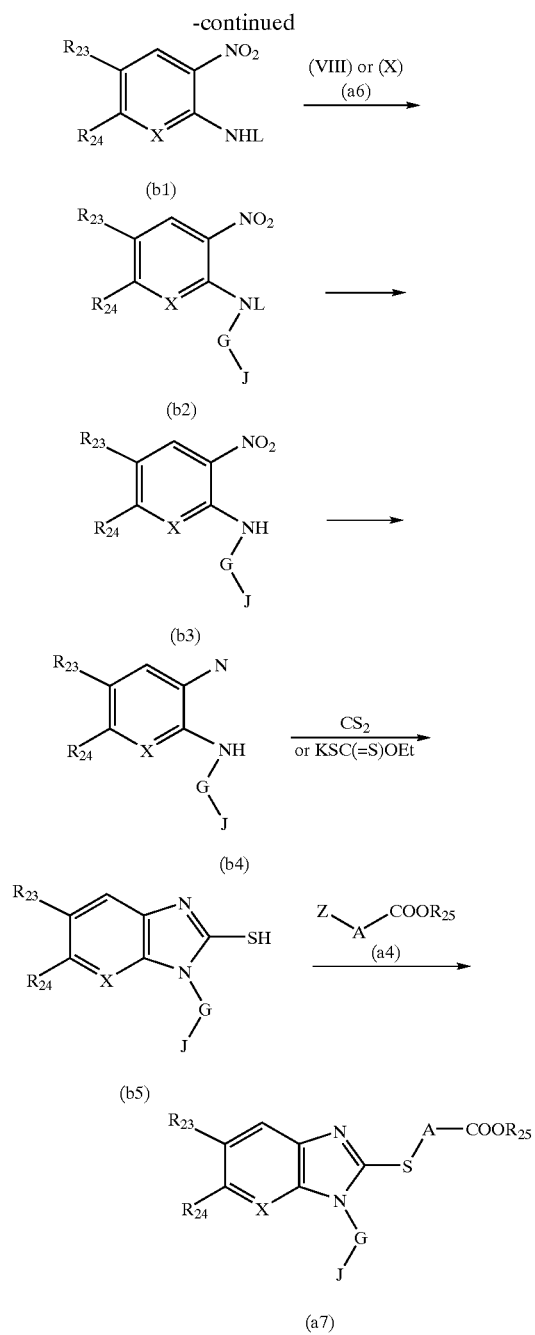

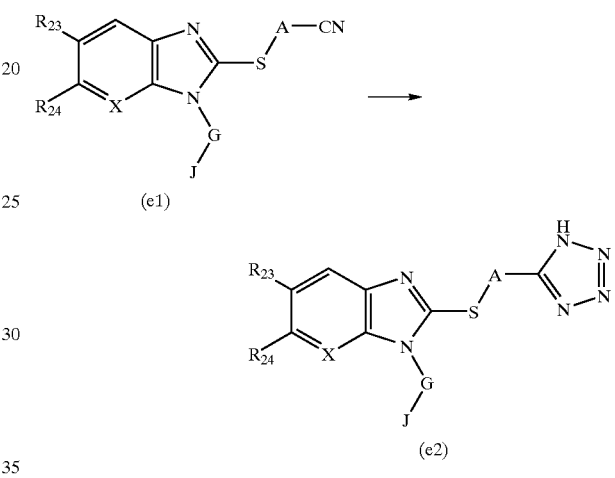

the halide derivative (a6). Trifluoroacetyl group, acetyl group, t-butoxycarbonyl group, benzyl group and the like can be cited as the protecting group L. The reaction of the o-phenylenediamine derivative (b4) with $CS_2$ can be carried out in the same manner as in the synthetic method (A) and the reaction with KSC(=S)OEt can be conducted according to the method described in, for example, Organic Synthesis (OS) 1963, Vol. 4, pp. 569–570. Other reactions can be carried out in the same manner as in the Synthetic method (A).

The benzimidazole derivatives (XX) in which E is tetrazol-5-yl and M is S can be prepared according to the following synthetic method (E).

Synthetic Method (E)

wherein, $R_{23}$, $R_{24}$, A, G, J and X are each the same as defined above.

The nitrile derivative (e1) is reacted with various azide compounds and converted into tetrazole derivatives (e2). Examples of azide compounds include Trialkyltin azide compounds such as trimethyltin azide, hydrazoic acid, its ammonium salt and the like. When the organotin azide compounds are used, the compounds are preferably used in a molar amount of about 1 to 4 times based on the compound (e1). When the hydrazoic acid or its ammonium salt is used, sodium azide and ammonium chloride or a tertiary amine such as triethylamine are preferably used in a molar amount of about 1 to 5 times based on the compound (e1). The each reaction is carried out at a temperature of 0 to 200° C. by using a solvent such as toluene, benzene or DMF.

Namely, the amino group of the 2-nitroaniline derivative (a1) is protected with an appropriate protecting group L to provide (b1), then (b1) is reacted with the halide derivative (a6) represented by the above formula (VIII) or the above formula (X) to obtain (b2). (b3) is obtained by removing protecting group L. The nitro group of (b3) is reduced to obtain an o-phenylenediamine derivative (b4), then (b4) is reacted with $CS_2$ or KSC(=S)OEt to provide a compound (b5). The resulting compound (b5) is then reacted with a halide ester derivative (a4). Thereby, the benzimidazole derivative (a7) can be obtained. The benzimidazole derivative (a7), if necessary, can be subjected to hydrolytic reaction to thereby obtain a benzimidazole derivative in which $R_{25}$ is a hydrogen atom.

The compound (b3) can directly be obtained by reacting the 2-nitroaniline derivative (a1) in an unprotected state with The benzimidazole derivatives (XX) in which M is SO or $SO_2$ can be prepared by the following synthetic method (F):

Synthetic Method (F)

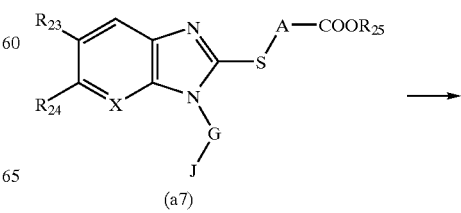

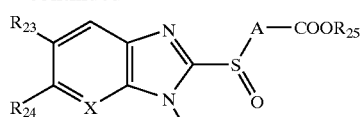

(f1)

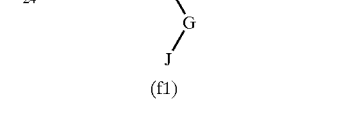

(f2)

wherein, $R_{23}$, $R_{24}$, $R_{25}$, A, G, J and X are each the same as defined above.

Namely, the benzimidazole compound (a7) is reacted with a peroxide compound in an appropriate solvent to provide a sulfoxide derivative (f1) and/or a sulfone derivative (f2). Examples of the peroxide compound to be used are perbenzoic acid, m-chloroperbenzoic acid, peracetic acid and hydrogen peroxide. For examples of a solvent to be used are chloroform and dichloromethane. The ratio of the peroxide compound to the compound (a7) used is not especially limited, and may suitably be selected within a wide range. Usually, the molar amount used is usually preferably about 1.2 to 5 times. The each reaction is carried out usually at about 0 to 50° C., preferably 0° C. to room temperature and usually completed in about 4 to 20 hours.

The benzimidazole derivative (XX) in which M is a single bond can be prepared according to the following synthetic method (G):

Synthetic Method (G)

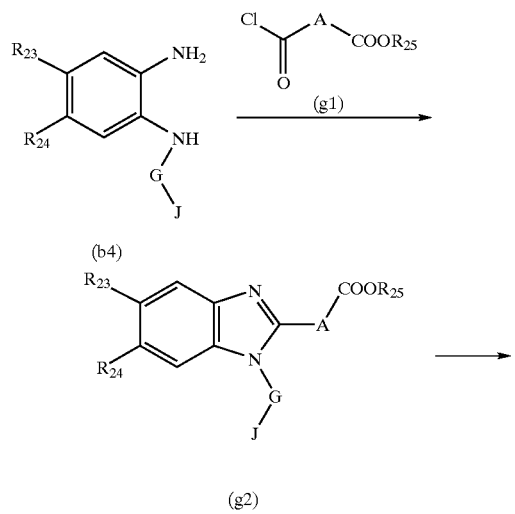

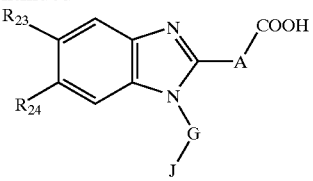

(g3)

wherein X, A, G, J and $R_{25}$ are each the same as defined above.

Namely, a known acid chloride derivative (g1) can be reacted with the diamine compound (b4) to obtain a benzimidazole derivative (g2). The —$COOR_{25}$ of the (g2), if necessary, can be hydrolyzed to provide a benzimidazole derivative (g3) in which $R_{25}$ is a hydrogen atom.

The cyclizing reaction is described in the Journal or Medicinal Chemistry (J. Med. Chem.), 1993, Vol. 36, pp. 1175–1187.

EXAMPLES

The present invention will be more detailed with the following examples, which are not intended to limit the scope of the present invention.

Example 1

Synthesis of 3-methyl-1-prop-2-ynylthiobenzene [General Formula (VI)]

A condenser, an internal thermometer, a mechanical stirrer and a dropping funnel were attached to a 5-L three-neck flask. Into the flask, were introduced 673 g of potassium carbonate and 1500 mL of methyl ethyl ketone. Into the dropping funnel, were introduced 500 g of m-toluenethiol and 200 mL of methyl ethyl ketone. Both were dropped in 10 minutes. The resulting mixture was intactly stirred at room temperature for 1 hour. The internal temperature was raised to 28° C. The three-neck flask was dipped in a water bath. Into the dropping funnel, were introduced 333 mL of propargyl bromide and 300 mL of methyl ethyl ketone. The dropping was then started. The dropping was carried out for 20 minutes while maintaining the internal temperature at about 55 to 65° C. by controlling the dropping. The stirring was intactly carried out under the water bath for 50 minutes. The resulting suspension of the reaction system was then directly filtered through a Buchner funnel, and the vessel and solids were washed with 900 mL of ethyl acetate. The obtained filtrate was subsequently vacuum concentrated. Further, 1500 mL of ethyl acetate, 2 L of water and 100 mL of 1 N HCl were added to separate an organic layer from an aqueous layer. The aqueous layer was extracted with 500 mL of ethyl acetate twice. The extract was washed with 1000 mL of a saturated brine twice and dried over anhydrous magnesium sulfate. After filtration, the filtrate was concentrated to provide 601.14 g of a crude substance (yield 92%, purity 88%). Only 300 g of the crude substance was distilled to obtain 239.68 g of 3-methyl-1-prop-2-ynylthiobenzene at 100 to 102° C./7 mmHg (recovery ratio 80%, purity>98%).

$^1$H-NMR (270 MHz, $CDCl_3$)δ (ppm): 7.36–7.03 (4H, m, Ar), 3.56 (2H, d, $CH_2$), 2.34, (3H, s, Me), 2.24 (1H, t, CH).

Example 2

Synthesis of 3-methyl-1-prop-2-ynylsulfinylbenzene [General Formula (VII)]

An internal thermometer, a mechanical stirrer and a 1-L dropping funnel were attached to a 10-L three neck flask.

Into the flask, it were introduced 427.78 g of sodium periodate, 2000 mL of water and 2000 mL of methanol. The resulting mixture was intactly stirred at room temperature for 1 hour. Since the sodium periodate was not completely dissolved, 2000 mL of water was further added. After confirming the complete dissolution of the sodium periodate, 3-methyl-1-prop-2-ynylthiobenzene (300.01 g) and methanol (1000 mL) were introduced into the dropping funnel and dropped in 30 minutes. The resulting mixture was stirred at room temperature. After 2 hours, the mixture was cooled with an ice bath taking 1 hour and then filtered through a Buchner funnel. The solids were thoroughly washed with 2 L of ethyl acetate, the resulting filtrate and 2 L of the ethyl acetate used for washing the solids were vacuum concentrated. The extraction of 4 L of an aqueous layer was carried out with 1000 mL of ethyl acetate three times. The organic layer was washed with 1000 mL of a saturated brine twice and then dried with anhydrous magnesium sulfate. After filtration, the filtrate was concentrated to obtain 314.45 g of an oil of 3-methyl-1-prop-2-ynylsulfinylbenzene. The resulting crude substance was converted into 3000 mL of a methanol solution and extracted with 3000 mL of hexane twice to thereby provide the objective substance 3-methyl-1-prop-2-ynylsulfinylbenzene of purity 98% or above (yield 79%, yield 248.42 g).

$^1$H-NMR (400 MHz, CDCl$_3$, ppm) 2.27 (s, 1H, CH), 2.37 (s, 3H, Me), 3.56 (abq, 2H, —CH$_2$—), 7.27 (dt, 1H, Ar), 7.34 (t, 1H, Ar), 7.41 (dt, 1H, Ar), 7.47 (dt, 1H, Ar).

Example 3

Synthesis of a Mixture of (4-methylbenzo[b]thiophen-3-yl)methyl 2,2,2-trifluoroacetate and (6-methylbenzo[b]thiophen-3-yl)methyl 2,2,2Trifluoroacetate [General Formula (V)]

An internal thermometer, a magnetic stirrer and a 1000-mL dropping funnel were attached to a 10-L three neck flask. Into the flask, was introduced 3000 mL of toluene. The flask was dipped in an oil bath at a bath temperature of 95° C. After confirming the internal temperature of 85° C., 3-methyl-1-prop-2-ynylsulfinylbenzene (251.25 g) dissolved in 700 mL of toluene was dropped taking 15 minutes. After completing the dropping, 500 mL of toluene was dropped in order to maintain the internal temperature between 85 and 95° C. The resulting mixture was cooled to 20° C. taking 1 hour from the time of 40 minutes after completing the dropping of the raw materials. The reaction vessel was dipped in an ice bath and trifluoroacetic anhydride (120 mL) was introduced into the dropping funnel. Dropping was carried out for 20 minutes in an ice bath. The mixture was intactly stirred at room temperature for 30 minutes. The reaction solution was slowly poured into 4 L of an aqueous saturated sodium hydrogencarbonate. An organic layer was separated from an aqueous layer, and the resulting aqueous layer was extracted with 500 mL of toluene. The organic layer was washed with 1500 mL of a saturated brine twice. The organic layer was dried with anhydrous magnesium sulfate, then filtered and concentrated to obtain an orange oil, a mixture (356.72 g) of (4-methylbenzo[b]thiophen-3-yl)methyl 2,2,2-trifluoroacetate and (6-methylbenzo[b]thiophen-3-yl) 2,2,2-trifuoroacetate.

$^1$H-NMR (400 MHz, CDCl$_3$, ppm) 2.47 (s, 4.5H), 2.72 (s, 3H), 5.56 (s, 2H,), 5.67 (s, 3H), 7.16–7.28 (m, 8H), 7.45 (s, 1.5H), 7.49 (s, 1H), 7.58–7.78 (m, 4H).

Example 4

Synthesis of a Mixture of (4-methylbenzo[b]thiophen-3-yl)methan-1-ol and (6-methylbenzo[b]thiophen-3-yl)methan-1-ol [General Formula (II) and General Formula (III)] by Hydrolytic Reaction A stirrer bar, a 100-mL dropping funnel and an internal thermometer were attached to a 300-mL three neck flask. In 100 mL of tetrahydrofuran, was dissolved 30.05 g of the mixture of 4-methylbenzo[b]thiophen-3-yl)methyl 2,2,2-trifluoroacetate and (6-methylbenzo[b]thiophen-3-yl)methyl 2,2,2-trifluoroacetate. The resulting solution was introduced into the flask and intactly cooled to an internal temperature of 20° C. Into the dropping funnel, was introduced a 1 N aqueous solution of sodium hydroxide (100 mL). The dropping was carried out for 10 minutes and the resulting mixture was intactly stirred at room temperature for 60 minutes. The reaction solution was introduced into a 500-mL separating funnel, and 300 mL of hexane was further added. The organic layer was directly separated from an aqueous layer. The resulting organic layer was washed with 500 mL of water three times and 500 mL of a saturated brine twice. The organic layer was dried with anhydrous magnesium sulfate, filtered and concentrated to obtain a brown oil, a mixture (28.24 g) of (4-methylbenzo[b]thiophen-3-yl)methan-1-ol and (6-methylbenzo[b]thiophen-3-yl)methan-1-ol.

Example 5

Purification-1 of (4-methylbenzo[b]thiophen-3-yl)methan-1-ol [General Formula (II)]

To the brown oil obtained in Example 4, was added 20 mL of ethyl acetate. The resulting mixture was stirred for 10 minutes. To the mixture, was then added 100 mL of hexane in three divided portions. The obtained mixture was intactly stirred for 2 hours, then filtered and dried to provide 8.33 g (yield 27.8%) of (4-methylbenzo[b]thiophen-3-yl)methan-1-ol which was a light orange crystal. The purity was 98%.

$^1$H-NMR (400 MHz, CDCl$_3$, ppm) 2.82 (s, 3H, 4-Me), 5.00 (s, 2H, —CH$_2$—OH), 7.10 (d, 1H, J$_{5,6}$=8 Hz, H-5), 7.24 (t, 1H, J$_{5,6}$=J$_{6,7}$=8 Hz, H-6), 7.40 (s, 1H, H-2), 7.70 (d, 1H, J$_{6,7}$=8 Hz, H-7).

$^{13}$C-NMR (100 MHz, CDCl$_3$, ppm) 20.8 (4-Me), 61.4 (—CH$_2$—OH), 120.8 (C-7), 122.6 (C-6), 124.5 (C-2), 126.2 (C-5), 133.7 (C-4), 136.2 (C-3a), 137.4 (C-3), 141.9 (C-7a).

Example 6

Synthesis of a Mixture of (4-ethylbenzo[b]thiophen-3-yl)methan-1-ol [General Formula (II)] and (6-methylbenzo[b]thiophen-3-yl)methan-1-ol [General Formula (III)] by Reductive Reaction A mechanical stirrer, a 200-mL dropping funnel and an internal thermometer were attached to a 3000-mL three neck flask. A solution obtained by dissolving the mixture (300.00 g) of the (4-methylbenzo[b]thiophen-3-yl)methyl 2,2,2-trifluoroacetate and the (6-methylbenzo[b]thiophen-3-yl) methyl 2,2,2-trifluoroacetate obtained by the reaction in Example 3 in 1500 mL of toluene was introduced into the flask, which was dipped in a water bath. Into the flask, was introduced 30.00 g of sodium borohydride. Methanol (150 mL) was introduced into the dropping funnel. The dropping was carried out for 60 minutes, and the mixture was intactly stirred at room temperature for 60 minutes. Water (1000 mL) was added to the flask and the resulting mixture was filtered through Celite. An organic layer was separated from an aqueous layer, and the aqueous layer was extracted with 500 mL of toluene. The organic layer was washed with 1000 mL of a saturated brine twice. The organic layers were dried with anhydrous magnesium sulfate, filtered and concentrated to obtain a yellow oil, a mixture (295.12 g) of the (4-methylbenzo[b]thiophen-3-yl)methan-1-ol and the (6-methylbenzo[b]thiophen-3-yl)methan-1-ol.

$^1$H-NMR (400 MHz, CDCl$_3$, ppm) 2.387 (s, 3H), 2.67 (s, 5H), 4.77 (s, 2H,), 4.87 (s, 3H), 7.02–7.16 (m, 6H), 7.55–7.63 (m, 5H).

Example 7

Purification-2 of (4-methylbenzo[b]thiophen-3-yl)methan-1-ol [General Formula (II)]

To the yellow oil obtained in Example 6, was added 100 mL of ethyl acetate. The resulting mixture was stirred for 10 minutes. To the mixture, was added 400 mL of hexane in four divided portions. The resulting mixture was intactly stirred for 2 hours, then filtered and dried to provide 80.05 g (yield 27%) of a white to a light yellow crystal (4-methylbenzo[b]thiophen-3-yl)methan-1-ol. The purity was 98% or above.

$^1$H-NMR (400 MHz, CDCl$_3$, ppm) 2.77(s, 3H, 4-Me), 4.99 (d, 2H, —CH$_2$—OH), 7.12 (dt, 1H, $J_{5,6}$=8 Hz, $J_{5, Me}$=0.8 Hz, H-5), 7.21 (t, 1H, $J_{5,6}$=$J_{6,7}$=8 Hz, H-6), 7.38 (s, 1H, H-2), 7.68 (dd, 1H, $J_{6,7}$=8 Hz, H-7).

Example 8

Purification-3 of (4-methylbenzo[b]thiophen-3-yl)methan-1-ol [General Formula (II)]

To 4.95 g of a mixture of (4-methylbenzo[b]thiophen-3-yl)methan-1-ol and (6-methylbenzo[b]thiophen-3-yl)methan-1-ol (a ratio of the 4-methyl derivative/6-methyl derivative=about 6/1), was added 25 mL of acetonitrile. The resulting mixture was refluxed, then cooled to room temperature and further cooled in a refrigerator overnight. The cooled mixture was then filtered, washed with acetonitrile and dried to obtain 3.15 g of a white to a light yellow crystal (4-methylbenzo[b]thiophen-3-yl)methan-1-ol (recovery ratio 64%). The purity was 99%.

$^1$H-NMR (400 MHz, CDCl$_3$, ppm): 2.82 (s, 3H, 4-Me), 5.00 (s, 2H, —CH$_2$—OH), 7.10 (d, 1H, $J_{5,6}$=8 Hz, H-5), 7.24 (t, 1H, $J_{5,6}$=$J_{6,7}$=8 Hz, H-6), 7.40 (s, 1H, H-2), 7.70 (d, 1H, $J_{6,7}$=8 Hz, H-7).

$^{13}$C-NMR (100 MHz, CDCl$_3$, ppm): 20.8 (4-Me), 61.4 (—$\underline{C}$H$_2$—OH), 120.8 (C-7), 122.6 (C-6), 124.5 (C-2), 126.2 (C-5), 133.7(C-4), 136.2 (C-3a), 137.4 (C-3), 141.9 (C-7a).

Example 9

Purification-4 of 4-methylbenzo[b]thiophen-3-yl)methan-1-ol [General Formula (II)]

To 26 g of a mixture of (4-methylbenzo[b]thiophen-3-yl)methan-1-ol and (6-methylbenzo[b]thiophen-3-yl)methan-1-ol (a ratio of the 4-methyl derivative/6-methyl derivative=about 4/3), was added 26 mL of toluene. The resulting mixture was refluxed and then cooled at room temperature. To the cooled mixture, was added 26 mL of hexane. The obtained mixture was stirred at room temperature overnight and then filtered. The resulting crystal was washed with 20 mL of toluene-hexane (1/1) and 10 mL of hexane and subsequently dried to provide 7.3 g of a white to a light yellow crystal, 4-methylbenzo[b]thiophen-3-yl)methan-1-ol (recovery ratio=28%). The purity was 99%.

$^1$H-NMR (200 MHz, CDCl$_3$, ppm): 2.79 (s, 3H, 4-Me), 5.01 (d, 2H, —CH$_2$—OH), 7.10–7.24 (m, 2H, H-5, H-6), 7.41 (s, 1H, H-2), 7.69 (d, 1H, $J_{6,7}$=8 Hz, H-7).

Example 10

Synthesis of 3-(bromomethyl)-4-methylbenzo[b]thiophene [General Formula (VIII)]

A magnetic stirrer, a 100-mL dropping funnel and an internal thermometer were attached to a 1-L three neck flask. In 200 mL of cyclohexane, was dissolved (4-methylbenzo[b]thiophen-3-yl)methan-1-ol (69.95 g). The resulting solution was introduced into the flask, and phosphorus tribromide (18 mL) was introduced into the dropping funnel. The phosphorus tribromide was dropped at room temperature taking 20 minutes (the internal temperature was raised to 30° C.). The obtained mixture was stirred at room temperature for 60 minutes and at 60° C. for 1 hour. The solution was added to ice water (1 L) to separate an organic layer from an aqueous layer. The resulting aqueous layer was extracted with 1 L of toluene. The organic layer was washed with a saturated aqueous sodium hydrogencarbonate (1 L) twice and washed with a saturated brine (1 L) twice. The organic layers were dried over anhydrous magnesium sulfate, then filtered and concentrated to obtain a light yellow solid (99.69 g). The resulting crude substance was recrystallized with 200 mL of hot cyclohexane to provide a white solid (52.19 g, yield 55%) of 3-(bromomethyl)-4-methylbenzo[b]thiophene.

$^1$H-NMR (400 MHz, CDCl$_3$, ppm) 2.90 (s, 3H, 4-Me), 4.89 (s, 2H, —CH$_2$—Br), 7.15 (d, 1H, $J_{5,6}$=8 Hz, H-5), 7.24 (t, 1H, $J_{5,6}$=$J_{6,7}$=8 Hz, H-6), 7.48 (s, 1H, H-2), 7.68 (d, 1H, $J_{6,7}$=8 Hz, H-7).

Example 11

Synthesis of 4-methyl-1-(prop-2-ynylsulfinyl)benzene [General Formula (XII)]

To 40 g (322 mmol) of p-toluenethiol, were added 200 mL of 2-butanone and 53.4 g (386 mmol) of potassium carbonate. The resulting mixture was cooled with ice, and 26.7 mL (354 mmol) of 1-bromo-propyne was added. The obtained mixture was stirred for 2 hours while cooling the reaction vessel with water. After 2 hours, the reaction system was filtered, and precipitates were washed with 50 mL of 2-butanone. The filtrate was vacuum concentrated to obtain 49.9 g of a yellow transparent oil 4-methyl-1-prop-2-ynylthiobenzene [general (XI)]. (crude yield: 96%).

$^1$H-NMR (270 MHz, CDCl$_3$)δ (ppm): 7.38 (2H, d, Ar), 7.06 (2H, d, Ar), 3.56 (2H, s, CH$_2$), 2.33, (3H, s, Me), 2.21 (1H, t, CH).

In 250 mL of water, was subsequently added and dissolved 68.7 g (321 mmol) of sodium periodate. A methanol solution (250 mL) of 49.6 g (306 mmol) of 4-methyl-1-prop-2-ynylthiobenzene [general formula (XI)] was dropped and stirred at room temperature for 2.5 hours. After 2.5 hours, the mixture was filtered, and the solids were washed with 100 mL of ethyl acetate. The filtrate was vacuum concentrated, and 200 mL of water was added. The resulting mixture was extracted with ethyl acetate (150 mL) three times. The obtained organic layers were washed with 150 mL of water, dried with magnesium sulfate and vacuum concentrated to provide 50.6 g (crude yield 93%) of 4-methyl-1-(prop-2-ynylsulfinyl)benzene.

$^1$H-NMR (270 MHz, CDCl$_3$)δ (ppm): 7.61 (2H, d, Ar), 7.34 (2H, d, Ar), 3.62 (2H, dd, CH$_2$), 2.33, (3H, s, Me), 2.32 (1H, t, CH).

Example 12

Synthesis of (prop-2-ynylsulfinyl)benzene [General Formula (XII)]

Thiophenol (55.34 g, 502.3 mmol) was dissolved in 150 mL of acetonitrile. Potassium carbonate (2.07 g, 15.0 mmol) was added, and the resulting mixture was dipped in a water bath. To the resulting mixture, was dropped 49.2 mL (652.9 mmol) of propargyl bromide taking 30 minutes. Further, 100 mL of acetonitrile was added. The obtained mixture was then stirred at room temperature for 1 hour and 20 minutes. After 1 hour and 35 minutes, propargyl bromide (3 mL) was added to further stir the mixture for 15 minutes. The mixture was then filtered, vacuum concentrated and vacuum dried to obtain 71.50 g of an oil. In 500 mL of methanol, was dissolved 70.50 g (0.476 mol) of the resulting oil. The obtained solution was added to 500 mL of an aqueous solution of sodium periodate (108.3 g, 0.506 mol), and the obtained mixture was stirred at room temperature. After 1 hour, the mixture was filtered and vacuum concentrated to separate a lower layer. The aqueous layer was extracted with ethyl acetate (250 mL×3). The organic layers and the lower layer were dried with Glauber's salt, vacuum concentrated and dried to synthesize 77.8 g of (prop-2-ynylsulfinyl) benzene. Crude yield was 96%.

$^1$H-NMR (270 MHz, CDCl$_3$)δ (ppm): 7.53–7.74 (5H, m, Ar), 3.65 (2H, ddd, CH$_2$), 2.35 (1H, t, CH).

Example 13

Synthesis of 3,5-dimethyl-1-(prop-2-ynylsulfinyl) benzene [General Formula (XII)]

In 20 mL of acetonitrile, was dissolved 5.56 g (40.2 mmol) of 3,5-dimethylbenzenethiol. To the resulting solution, were successively added 3.63 mL (48.3 mmol) of propargyl bromide and 6.91 g (50 mmol) of potassium carbonate. The obtained mixture was then refluxed. After 1 hour, the mixture was filtered, vacuum concentrated and vacuum dried to obtain 7.79 g of an oil, which was then dissolved in 70 mL of methanol. To the resulting solution, was dropped 40 mL of an aqueous solution of sodium periodate (9.19 g, 43 mmol). Furthermore, 30 mL of methanol and 20 mL of water were added, and the resulting mixture was stirred at room temperature. After 1.5 hours, the mixture was filtered, and precipitates were washed with methanol. The washed methanol was vacuum concentrated, and the aqueous layer was extracted with ethyl acetate (100 mL×2). The organic layers were dried with Glauber's salt, vacuum concentrated and dried to provide 7.66 g of 3,5-dimethyl-1-(prop-2-ynylsulfinyl)benzene. The crude yield was 99%.

$^1$H-NMR (270 MHz, CDCl$_3$)δ (ppm): 7.31 (2H, s, Ar), 7.15 (1H, s, Ar), 3.63 (2H, t, CH$_2$), 2.39 (6H, 2, Me), 2.35 (1H, t, CH).

Example 14

Synthesis of 5-methyl-3-methylene-2-hydrobenzo[b] thiophen-2-ol [General Formula (IX)]

In 1.6 mL of propyl acetate, was dissolved 107.0 mg (0.6 mmol) of the compound obtained in Example 11. The resulting solution was refluxed for 20 minutes and subsequently vacuum concentrated and dried to obtain 108.5 mg of 5-methyl-3-methylene-2-hydrobenzo[b]thiophen-2-ol. The crude yield was 105%.

$^1$H-NMR (400 MHz, CDCl$_3$)δ (ppm): 7.24 (1H, s, Ar), 7.05 (2H, s, Ar), 6.17 (1H, d, CH) 5.78 (1H, s, =CH), 5.49 (1H, s, =CH), 2.30 (3H, s, Me).

Example 15

Synthesis of 3-methylene-2-hydrobenzo[b]thiophen-2-ol [General Formula (IX)]

In 4.5 mL of dioxane, was dissolved 301 mg of the compound obtained in Example 12. The resulting solution was heated at 100° C. for 2 hours. After cooling, the solution was vacuum concentrated to synthesize 292 mg of a yellow transparent oil 3-methylene-2-hydrobenzo[b]thiophen-2-ol.

$^1$H-NMR (270 MHz, CDCl$_3$)δ (ppm): 7.06–7.48 (4H, m, Ar), 6.15 (1H, d, CH), 5.84 (1H, s, =CH), 5.55 (1H, s, =CH), 2.45 (3H, s, Me).

Example 16

Synthesis of 4,6-dimethyl-3-methylene-2-hydrobenzo[b]thiophen-2-ol [General Formula (IX)]

In 2 mL of propyl acetate, was dissolved 117.6 mg (0.61 mmol) of the compound obtained in Example 13. The solution was refluxed for 20 minutes. After cooling, the solution was vacuum concentrated and dried to synthesize 2,3-dihydro-4,6-dimethyl-3-methylene-benzo[b]thiophen-2-ol. The crude yield was 95%.

$^1$H-NMR (400 MHz, CDCl$_3$)δ (ppm): 6.89 (1H, s, Ar), 6.72 (1H, s, Ar), 5.94 (1H, d, CH) 5.69 (1H, s, =CH), 5.61 (1H, s, =CH), 2.43 (3H, s, Me), 2.26 (3H, s, Me).

Example 17

Synthesis of 3-(bromomethyl)-5-methylbenzo[b] thiophene [General Formula (X)]

In 1 mL of propyl acetate, was dissolved 71.9 mg (0.40 mml) of the compound obtained in Example 14. To the resulting solution, was added 0.0569 mL (0.5 mmol) of a 48% hydrobromic acid. The obtained mixture was allowed to stand at room temperature for 20 minutes. To the mixture, was added 3 mL of ethyl acetate. The obtained mixture was washed with water, and the organic layer was dried with magnesium sulfate, vacuum filtered and dried to obtain 88.2 mg of 3-(bromomethyl)-5-methylbenzo[b]thiophene. The yield was 91%.

$^1$H-NMR (270 MHz, CDCl$_3$)δ (ppm): 7.68 (1H, d, H-7), 7.65 (1H, s, H-4), 7.41 (1H, s, H-2), 7.15 (1H, dd, H-6), 4.67 (2H, s, CH$_2$), 2.45 (3H, s, Me).

Example 18

Synthesis of 3-(chloromethyl)-benzo[b]thiophene [General Formula (X)]

In 4 mL of propyl acetate, was dissolved 270 mg (1.64 mmol) of the compound obtained in Example 15. To the resulting solution, was added 0.0615 mL (2.46 mmol) of a 4 M hydrogen chloride dioxane solution. The obtained mixture was allowed to stand at room temperature for 30 minutes. The mixture was then concentrated, and 10 mL of water was added. The resulting mixture was extracted with ethyl acetate, and the organic layer was dried with magnesium sulfate, vacuum filtered and dried to provide 271 mg of 3-(chloromethyl)-benzo[b]thiophene. The yield was 90%.

$^1$H-NMR(270 MHz, CDCl$_3$)δ (ppm):7.88–7.90 (2H, m, Ar), 7.30–7.50 (3H, m, Ar), 4.86(2H, s, CH$_2$).

Example 19 Synthesis of 3-(bromomethyl)-4,6-dimethylbenzo[b]thiophene [General Formula (X)]

In 1 mL of propyl acetate, was dissolved 55.3 mg of the compound obtained in Example 16. To the resulting solution, was added 39.9 μL of a 48% hydrobromic acid. The obtained mixture was allowed to stand at room temperature. After 20 minutes, 3 mL of ethyl acetate was added. The resulting mixture was washed with water, dried with magnesium sulfate, vacuum concentrated and dried to synthesize 3-(bromomethyl)-4,6-dimethylbenzo[b]thiophene. The yield was 90%.

$^1$H-NMR (270 MHz, CDCl$_3$)δ (ppm): 7.40 (1H, d, H-5), 7.33 (1H, s, H-5), 6.92 (1H, s, H-2), 4.81 (2H, s, CH$_2$), 2.81 (3H, s, 4-Me), 2.34 (3H, s, 6-Me).

Example 20

Synthesis of 3-(chloromethyl)-5-methylbenzo[b]thiophene [General Formula (X)]

In 15 mL of dioxane, was dissolved 873.4 mg (4.9 mmol) of the compound obtained in Example 11. The resulting solution was stirred with heating at 100° C. for 70 minutes. The reaction system was cooled to room temperature, and 1.5 mL (6 mmol) of a 4 M hydrogen chloride-dioxane was added. The resulting mixture was stirred at room temperature for 1 hour. The reaction system was vacuum concentrated, and was added 0.80 mL of cyclohexane. The obtained mixture was heated at 70° C. for 10 minutes and cooled to room temperature. The resulting precipitates were filtered to obtain 590.6 mg of 3-(chloromethyl)-5-methylbenzo[b]thiophene. The yield was 61%.

Calculated value=196.70. Analytical value m/z=196 [M+].

Example 21

Synthesis of 3-(bromomethyl)-5-methylbenzo[b]thiophene [General Formula (X)]

In 110 mL of dioxane, was dissolved 7.18 g (40.3 mmol) of the compound obtained in Example 11. The resulting solution was refluxed at 100° C. for 100 minutes The refluxed solution was then cooled, and 7.42 g (44 mmol) of a 48% hydrobromic acid was added. The obtained mixture was allowed to stand at room temperature for 1 hour. Water was then added, and the obtained mixture was extracted with ethyl acetate. The resulting extract was dried with magnesium sulfate and vacuum concentrated to provide 9.04 g of 3-(bromomethyl)-5-methylbenzo[b]thiophene. The yield was 93%.

Calculated value=241.10. Analytical value m/z=241 [M+].

Example 22

Synthesis of 3-(bromomethyl)-5-methylbenzo[b]thiophene [General Formula (X)]

In 445 mL of propyl acetate, was dissolved the compound obtained in Example 11 (29.7 g, 167 mmol). The resulting solution was heated at 100° C. for 1 hour. The solution was then cooled with ice to keep the internal temperature of the reaction system at 10° C. To the cooled solution, was added 22.8 mL of a 48% hydrobromic acid. The obtained mixture was allowed to stand under cooling with ice for 1 hour and 30 minutes. The aqueous layer was separated, and the organic layer was washed with 50 mL of water, dried with magnesium sulfate, vacuum concentrated and dried to obtain 35.3 g of a brown transparent oil 3-(bromomethyl)-5-methylbenzo[b]thiophene. (yield=88%).

$^1$H-NMR (270 MHz, CDCl$_3$)δ (ppm): 7.74 (1H, d, H-7), 7.68 (1H, s, H-4), 7.47 (1H, s, H-2), 7.23 (1H, dd, H-6), 4.73 (2H, s, CH$_2$), 2.51(3H, s, Me).

Example 23

Synthesis of 3-(chloromethyl)-benzo[b]thiophene [General Formula (X)]

In 50 mL of 1,4-dioxane, was dissolved 5.02 g (30.6 mmol) of the compound obtained in Example 12. The resulting solution was heated at 100° C. After 5 hours and 30 minutes, the solution was cooled to keep the internal temperature of the reaction system at 10° C. To the cooled solution, was subsequently added 8.42 mL (33.7 mmol) of a 4 M hydrogen chloride-dioxane solution. The obtained mixture was allowed to stand at room temperature. After 15 minutes, the reaction liquid was concentrated and dissolved in 50 mL of ethyl acetate. The resulting solution was washed with 40 mL of water. The organic layer was dried with magnesium sulfate. After concentrating, the concentrate was redissolved in 50 mL of ethyl acetate in order to remove the dioxane. The obtained solution was washed with 40 mL of water three times. The organic layer was dried over magnesium sulfate and vacuum concentrated to provide 5.18 g of 3-(chloromethyl)-benzo[b]thiophene. The yield was 93%.

$^1$H-NMR (270 MHz, CDCl$_3$)δ (ppm): 7.91–7.85 (2H, m, Ar), 7.36–7.48 (3H, m, Ar), 4.85 (2H, t, CH$_2$).

Example 24

Synthesis of 3-(bromomethyl)-4,6-dimethylbenzo[b]thiophene [General Formula (X)]

In 40 mL of propyl acetate, was dissolved 2.26 g (11.7 mmol) of the compound obtained in Example 13. The refluxing was carried out for 30 minutes. The solution was then cooled, and 1.59 mL (14 mmol) of a 48% hydrobromic acid was added. The resulting mixture was allowed to stand at room temperature for 30 minutes. Ethyl acetate was subsequently added, and the obtained mixture was washed with water, dried with magnesium sulfate and vacuum concentrated to obtain 2.49 g of 3-(bromomethyl)-4,6-dimethylbenzo[b]thiophene. The yield was 84%.

$^1$H-NMR (270 MHz, CDCl$_3$)δ (ppm): 7.46 (1H, s, H-5), 7.38 (1H, s, H-7), 6.98 (1H, s, H-2), 4.85 (2H, s, CH$_2$), 2.85 (3H, s, 4-Me), 2.40 (3H, s, 6-Me).

Comparative Example

Procedures were carried out as follows under reported conditions according to J. Chem. Soc., Chem. Comm., 848 (1974).

In 3 mL (an amount of 15 times) of dioxane, was dissolved 218.4 mg of 3-methyl-phenyl-propargyl-sulfoxide. The resulting solution was refluxed for 2 hours and 30 minutes. To the solution, were added 1 mL of water and 21.7 mg of p-toluenesulfonic acid monohydrate. The resulting mixture was heated at 70° C. for 2 hours. In this stage, a spot of a main product was confirmed with Rf=0.23 and spots of by-products were confirmed with Rf=0.41, 0.55, 0.70 and 0.83 in TLC (hexane-ethyl acetate=5:1). After vacuum concentration, water was added, and extraction with ethyl acetate was conducted. The organic layer was dried with magnesium sulfate and vacuum concentrated to provide 280.1 mg of a residue. The resulting residue was purified by thin-layer chromatography (using two 1. 13794 PLC plates 20×20 cm silica gel 60 0.5 mm, manufactured by Merck & Co., Inc.; developing system: hexane-ethyl acetate=5:1) to recover a fraction of the main product. Thereby, 131.5 mg of brown oil was obtained. The ratio of the 3-hydroxy-4-methyl-benzo[b]thiophene to the 3-hydroxy-6-methyl-benzo[b]thiophene proved to be about 3:2 from $^1$H-NMR and two-dimensional NMR of the fraction. Further, the fraction was only partially solidified even by allowing the fraction to stand, and the 3-hydroxy-4-methyl-benzo[b]thiophene could not be isolated.

$^1$H-NMR (270 MHz, CDCl$_3$)δ (ppm): 7.12–7.75 (11H, m, Ar, 4-Me-deriv., 6-Me-deriv.), 5.00 (3H, s, CH$_2$, 4-deriv.), 4.90 (2H, s, CH$_2$, 6-deriv.), 2.79 (4.5H, s, Me, 4-deriv.), 2.47 (3H, s, Me, 6-deriv.), 1.77 (2H, brs, OH, 4-Me-deriv.,

INDUSTRIAL APPLICABILITY

According to the present invention, 4-substituted-3-hydroxymethyl-benzo[b]thiophene derivatives useful as raw materials for medicines can be provided. Since the synthetic methods in the present invention are selective and the preparation can be carried out in high yield, the industrial value of the present invention is great. Furthermore, 3-halomethyl-benzo[b]thiophene derivatives can simply be synthesized from substituted benzenethiols in short steps and the present invention is industrially excellent.

What is claimed is:

1. 3,4-Disubstituted-benzo[b]thiophene derivatives represented by the following formula (I):

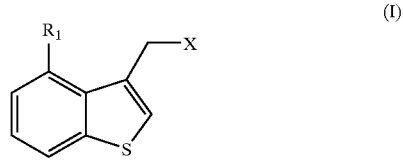

wherein, R$_1$ represents a halogen atom, a trihalomethyl group, a C$_{1-4}$ alkyl group or a C$_{1-4}$ alkoxy group; and X represents a hydroxy group or a halogen atom.

2. The 4-substituted-3-hydroxymethyl-benzo[b]thiophene derivatives according to claim 1, wherein X is a hydroxy group in the above formula (I).

3. The 3-hydroxymethyl-4-methyl-benzo[b]thiophene derivatives according to claim 2, wherein R$_1$ is a methyl group in the above formula (I).

4. The 4-substituted-3-halomethyl-benzo[b]thiophene derivatives according to claim 1, wherein X is a halogen in the above formula (I).

5. The 3-bromomethyl-4-methyl-benzo[b]thiophene derivatives according to claim 1, wherein R$_1$ is a methyl group; and X is a bromine atom in the above formula (I).

6. A process for obtaining benzo[b]thiophene derivatives represented by the following formula (II) comprising crystallizing a mixture comprising the benzo[b]thiophene derivatives represented by the following formula (II):

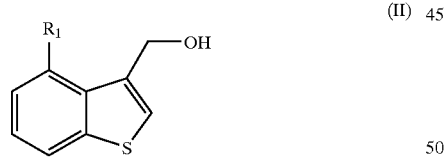

wherein, R$_1$ represents a halogen atom, a trihalomethyl group, a C$_{1-4}$ alkyl group or a C$_{1-4}$ alkoxy group, and benzo[b]thiophene derivatives represented by the following formula (III):

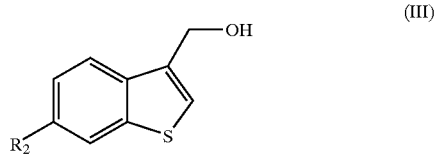

wherein, R$_2$ represents a halogen atom, a trihalomethyl group, a C$_{1-4}$ alkyl group or a C$_{1-4}$ alkoxy group, in a solvent.

7. The process for preparing benzo[b]thiophene derivatives according to claim 6, wherein the solvent for crystallization is a mixed solvent of a C$_{5-8}$ straight-chain, cyclic or branched hydrocarbon and a C$_{2-6}$ carboxylic acid ester, a mixed solvent of the C$_{5-8}$ straight-chain, cyclic or branched hydrocarbon and a C$_{6-8}$ aromatic hydrocarbon, or acetonitrile.

8. The process for preparing benzo[b]thiophene derivatives represented by the following formula (V):

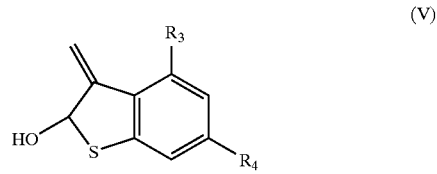

wherein, R$_3$ and R$_4$ are each the same as in the following formula (IV); and R$_5$ represents a hydrogen atom, a C$_{1-3}$ alkyl group or a trifluoromethyl group, comprising reacting compounds represented by the following formula (IV):

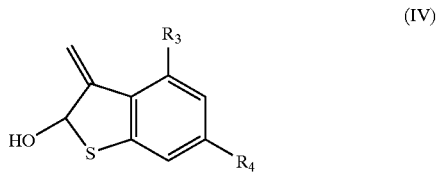

wherein, R$_3$ represents a hydrogen atom, and R$_4$ represents a halogen atom, a trihalomethyl group, a C$_{1-4}$ alkyl group or a C$_{1-4}$ alkoxy group; or R$_3$ represents a halogen atom, a trihalomethyl group, a C$_{1-4}$ alkyl group or a C$_{1-4}$ alkoxy group, and R$_4$ represents a hydrogen, with one kind or two or more kinds of C$_{1-4}$ carboxylic acids, their carboxylic acid anhydrides, trifluoroacetic acid, its trifluoroacetic anhydride.

9. The process for preparing a benzo[b]thiophene derivative according to claim 8, wherein R$_5$ is a trifluoromethyl group in the above formula (V).

10. A process for preparing the benzo[b]thiophene derivatives represented by the above formula (II) or the benzo[b]thiophene derivatives represented by the above formula (III) comprising subjecting the compounds represented by the above formula (V) to reduction with a metal hydride complex compound, basic hydrolysis, or acidic hydrolysis.

11. The process for preparing the benzo[b]thiophene derivatives represented by the above formula (II) or the above formula (III) according to claim 10, wherein the compounds represented by the above formula (V) are reduced with sodium borohydride.

12. A process for preparing the 4-substituted-3-hydroxymethyl-benzo[b]thiophene derivatives represented by the above formula (II) comprising:

introducing a propargyl group into m-substituted benzenethiols, providing compounds represented by the following formula (VI):

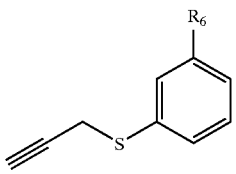

(VI)

wherein, $R_6$ represents a halogen atom, a trihalomethyl group, a $C_{1-4}$ alkyl group or a $C_{1-4}$ alkoxy group;

oxidizing the compounds represented by the formula (VI), obtaining compounds represented by the following formula (VII):

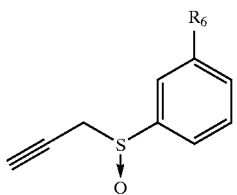

(VII)

wherein, $R_6$ is the same as defined in the above formula (VI);

subjecting the compounds represented by the formula (VII) to thermal rearrangement reaction, providing the compounds represented by the above formula (IV);

reacting the resulting compounds represented by the formula (IV) with one kind or two or more kinds of $C_{1-4}$ carboxylic acids, their carboxylic acid anhydrides, trifluoroacetic acid, or its trifluoroacetic anhydride, thereby obtaining the compounds represented by the above formula (V);

converting the ester group of the compounds represented by the formula (V) into a hydroxy group; and crystallizing the resulting mixture of the benzo[b]thiophene derivatives represented by the above formula (II) and the benzo[b]thiophene derivatives represented by the above formula (III) in a solvent.

13. The process for preparing the 3-hydroxymethyl-4-methyl-benzo[b]thiophene derivatives according to claim 12, wherein $R_6$ is a methyl group in the above formula (VI).

14. A process for preparing the 4-substituted-3-halomethyl-benzo[b]thiophene derivatives represented by the following formula (VIII):

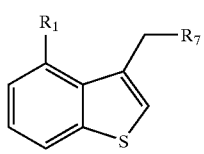

(VIII)

wherein, $R_1$ represents a halogen atom, a trihalomethyl group, a $C_{1-4}$ alkyl group or a $C_{1-4}$ alkoxy group; and $R_7$ represents a halogen atom, comprising converting the hydroxy group of the 4-substituted-3-hydroxymethyl-benzo[b]thiophene derivatives represented by the above formula (II), into a halogen atom.

15. A process for preparing the 4-methyl-3-halomethyl-benzo[b]thiophene derivatives according to claim 14, wherein $R_1$ is a methyl group in the above formula (VIII).

16. A process for preparing the 3-halomethyl-benzo[b]thiophene derivatives represented by the following formula (X):

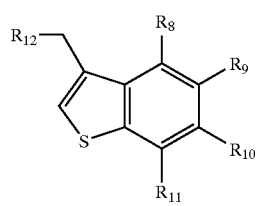

(X)

wherein, $R_8$ to $R_{11}$ are each the same as defined in the general formula (IX); and $R_{12}$ represents a halogen atom, comprising reacting compounds represented by the following formula (IX):

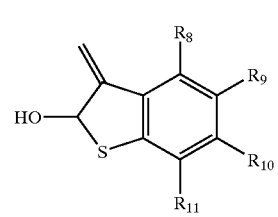

(IX)

wherein, $R_8$ to $R_{11}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group, with an equivalent amount or more of an acid.

17. A process for preparing the compounds represented by the above formula (X) comprising:

introducing a propargyl group into substituted benzenethiols, providing compounds represented by the following formula (XI):

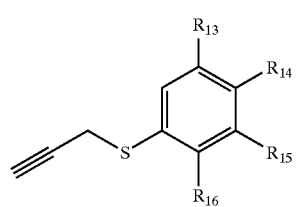

(XI)

wherein, $R_{13}$ and $R_{15}$ represent simultaneously and $R_{14}$ represents independently a hydrogen atom, a halogen atom, a trihalomethyl group, a cyano group, a $C_{1-4}$ alkyl group, a $C_{1-4}$ alkoxy group, a $C_{1-4}$ alkythio group, a $C_{1-4}$ acyloxy group, a $C_{1-4}$ acylamino group, or a trihalomethoxy group; and $R_{16}$ represents a hydrogen atom: or $R_{16}$ represents a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group; and $R_{13}$ to $R_{15}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group;

oxidizing the resulting compounds represented by the formula (XI), providing compounds represented by the following formula (XII):

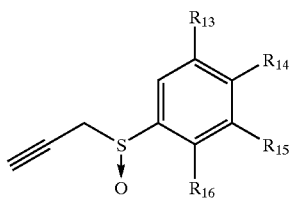

(XII)

wherein, $R_{13}$ to $R_{16}$ are each the same as in the above formula (XI);

subjecting the resulting compounds represented by the above formula (XII) to thermal rearrangement reaction, obtaining the compounds represented by the above formula (IX); and reacting the resulting compounds represented by the formula (IX) with an equivalent amount or more of an acid.

18. The process for preparation the compounds according to claim 16 or claim 17, wherein $R_8$ and $R_{10}$ in the above formula (IX) and the above formula (X) represent simultaneously and $R_9$ represents independently a hydrogen atom or a $C_{1-4}$ alkyl group and $R_{11}$ represents a hydrogen atom; or $R_{11}$ represents a $C_{1-4}$ alkyl group and $R_8$ to $R_{10}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group; and $R_{13}$, $R_{14}$ and $R_{15}$ in the above formula (XI) and the above formula (XII) represent simultaneously and $R_{14}$ represents independently a hydrogen atom or a $C_{1-4}$ alkyl group; and $R_{16}$ represents a hydrogen atom; or $R_{16}$ represents a $C_{1-4}$ alkyl group and $R_{13}$, $R_{14}$ and $R_{15}$ represent simultaneously or each independently a hydrogen atom, a halogen atom, a trihalomethyl group, a cyano group, a $C_{1-4}$ alkyl group, a $C_{1-4}$ alkoxy group, a $C_{1-4}$ alkylthio group, a $C_{1-4}$ acyloxy group, a $C_{1-4}$ acylamino group, or a trihalomethoxy group.

19. The process for preparation the compounds according to claim 18, wherein $R_{12}$ is a chlorine atom or a bromine atom in the above formula (X).

20. A process for preparing benzimidazole derivatives represented by the general formula (XX):

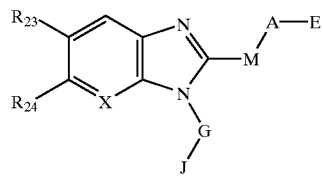

(XX)

in the formula (XX), $R_{23}$ and $R_{24}$ represent simultaneously or each independently a hydrogen atom, a halogen atom, a trihalomethyl group, a cyano group, a hydroxy group, a $C_{1-4}$ alkyl group or a $C_{1-4}$ alkoxy group; or $R_{23}$ and $R_{24}$ together represent —O—$CH_2$—O—, —O—$CH_2CH_2$—O— or —$CH_2CH_2CH_2$— (in this case, the each carbon atom may be substituted with one or plural $C_{1-4}$ alkyl groups);

A represents a substituted or an unsubstituted $C_{1-7}$ straight-chain, cyclic or branched alkylene group or alkenylene group which may be interrupted by one or more of —O—, —S—, —$SO_2$— and —$NR_{25}$— (wherein, $R_{25}$ represents a hydrogen atom or a $C_{1-6}$ straight-chain or branched alkyl group); the substituents which can be possessed by the groups are each a halogen atom, a hydroxy group, a nitro group, a cyano group, a straight-chain or branched $C_{1-6}$ alkyl group, a straight-chain or branched $C_{1-6}$ alkoxy group (including the case where two adjacent groups form an acetal bond, namely including the case in which the alkyl portions of geminal two alkoxy groups are connected to form a ring), a straight-chain or branched $C_{1-6}$ alkylthio group, a straight-chain or branched $C_{1-6}$ alkylsulfonyl group, a straight-chain or branched $C_{1-6}$ acyl group, a straight-chain or branched $C_{1-6}$ acylamio group, a trihalomethyl group, a trihalomethoxy group, a phenyl group, an oxo group, or a phenoxy group which may be substituted with one or more halogen atoms; the one or plural substituents may independently be substituted at optional positions of the alkylene group or alkenylene group except that hydroxy group and phenyl group are simultaneously substituted at the carbon of A which is bound to M that be a single bond in the formula (XX);

E represents a —$COOR_{25}$, a —$SO_3R_{25}$, a —$CONHR_{25}$, a —$SO_2NHR_{25}$, a tetrazol-5-yl group, a 5-oxo-1,2,4-oxadiazol-3-yl group or a 5-oxo-1,2,4-thiadiazol-3-yl group (where, $R_{25}$ is as defined above);

M represents a single bond or —$S(O)_m$—; where m is an integer of 0 to 2;

G and J represent each the above formula (I) or the above formula (X), with the proviso that G represents a methylene group in the 3-position of the benzothiophene represented by the above formula (X), and X of the above formula (I) and $R_{12}$ of the above formula (X) are each replaced with the nitrogen atom on the benziidazole ring; and X represents —CH= or a nitrogen atom, from the compounds represented by the above formula (I) prepared by the process for preparation according to any one of claims 6 or 8 or the compounds represented by the above formula (X) prepared by the process for preparation according to any one of claims 16 or 17.

* * * * *